United States Patent
Song et al.

(10) Patent No.: US 11,589,840 B2
(45) Date of Patent: Feb. 28, 2023

(54) METHODS FOR SUPER-RESOLUTION ULTRASOUND IMAGING OF MICROVESSELS

(71) Applicant: Mayo Foundation for Medical Education and Research, Rochester, MN (US)

(72) Inventors: Pengfei Song, Champaign, IL (US); Joshua D. Trzasko, Rochester, MN (US); Armando Manduca, Rochester, MN (US); Shigao Chen, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 217 days.

(21) Appl. No.: 16/617,628

(22) PCT Filed: May 30, 2018

(86) PCT No.: PCT/US2018/035147
§ 371 (c)(1),
(2) Date: Nov. 27, 2019

(87) PCT Pub. No.: WO2018/222724
PCT Pub. Date: Dec. 6, 2018

(65) Prior Publication Data
US 2020/0178939 A1 Jun. 11, 2020

Related U.S. Application Data

(60) Provisional application No. 62/512,847, filed on May 31, 2017.

(51) Int. Cl.
*A61B 8/08* (2006.01)
*A61B 8/06* (2006.01)
*G06T 7/00* (2017.01)

(52) U.S. Cl.
CPC .............. *A61B 8/5223* (2013.01); *A61B 8/06* (2013.01); *A61B 8/085* (2013.01); *A61B 8/0891* (2013.01);
(Continued)

(58) Field of Classification Search
CPC ......... A61B 8/5223; A61B 8/06; A61B 8/085; A61B 8/0891; A61B 8/481; A61B 8/5269;
(Continued)

(56) References Cited

U.S. PATENT DOCUMENTS 6,004,270 A 12/1999 Urbano et al.
2003/0229285 A1 12/2003 Simpson et al.
(Continued)

OTHER PUBLICATIONS

Jonas et al., Microfluidic characterization of cilia-driven fluid flow using optical coherence tomography-based particle tracking velocimetry, Biomedical Optics Express, Jul. 1, 2011, vol. 2, No. 7.*
(Continued)

*Primary Examiner* — Bo Joseph Peng
(74) *Attorney, Agent, or Firm* — Quarles & Brady LLP

(57) ABSTRACT

Systems and methods for super-resolution ultrasound imaging of microvessels in a subject are described. Ultrasound data are acquired from a region-of-interest in a subject who has been administered a microbubble contrast agent. The ultrasound data are acquired while the microbubbles are moving through, or otherwise present in, the region-of-interest. The region-of-interest may include, for instance, microvessels or other microvascuiature in the subject. By isolating, localizing, tracking, and accumulating the microbubbles in the ultrasound data, super-resolution images of the microvessels can be generated.

59 Claims, 14 Drawing Sheets

(52) U.S. Cl.
 CPC ............ *A61B 8/481* (2013.01); *A61B 8/5269* (2013.01); *G06T 7/0016* (2013.01); *G06T 2207/10132* (2013.01); *G06T 2207/30104* (2013.01)

(58) Field of Classification Search
 CPC ................... A61B 8/52; G06T 7/0016; G06T 2207/10132; G06T 2207/30104
 See application file for complete search history.

(56) References Cited

U.S. PATENT DOCUMENTS

| | | |
|---|---|---|
| 2018/0220997 A1 | 8/2018 | Song |
| 2019/0053780 A1 | 2/2019 | Song |

OTHER PUBLICATIONS

Alex Grinman, The Hungarian Algorithm for Weighted Bipartite Graphs, 18.434: Seminar in Theoretical Computer Science Apr. 30, 2015.*

Song et al. Improved Super-Resolution Ultrasound Microvessel Imaging with Spatiotemporal Nonlocal Means Filtering and Bipartite Graph-Based Microbubble Tracking, IEEE Trans Ultrason Ferroelectr Freq Control. Feb. 2018 ; 65(2): 149-167.*

Betzig, E. et al, "Imaging intracellular fluorescent proteins at nanometer resolution," Science, vol. 313, pp. 1642-1645, Sep. 15, 2006.

Bullitt, E. et al, "Measuring tortuosity of the intracerebral vasculature from MRA images," IEEE Trans Med Imaging, vol. 22, pp. 1163-1171, Sep. 2003.

Candes, E. et al, "Fast discrete curvelet transforms," Multiscale Modeling & Simulation, vol. 5, pp. 861-899, 2006.

Christensen-Jeffries, K. et al, "In vivo acoustic super-resolution and super-resolved velocity mapping using microbubbles," IEEE Trans Med Imaging, vol. 34, pp. 433-440, Feb. 2015.

Coupe, P. et al, "Nonlocal means-based speckle filtering for ultrasound images," IEEE transactions on image processing : a publication of the IEEE Signal Processing Society, vol. 18, pp. 2221-2229, Oct. 2009.

Frinking, P. J. A. et al, "Scattering properties of encapsulated gas bubbles at high ultrasound pressures," Journal of the Acoustical Society of America, vol. 105, pp. 1989-1996, Mar. 1999.

Hess, S.T. et al, "Ultra-high resolution imaging by fluorescence photoactivation localization microscopy," Biophys J, vol. 91, pp. 4258-4272, Dec. 1, 2006.

Kuhn H.W., "The Hungarian method for the assignment problem," Naval Research Logistics Quarterly, vol. 2, pp. 83-97, 1955.

International Search Report and Written Opinion from parent PCT/US2018/035147, dated Oct. 22, 2018, 22 pages.

Errico, et al., Ultrafast ultrasound localization microscopy for deep super-resolution vascular imaging, Nature, vol. 527, No. 7579, Nov. 26, 2015, pp. 499-502.

Song, et al., Ultrasound Small Vessel Imaging With Block-Wise Adaptive Local Clutter Filtering, IEEE Transactions on Medical Imaging, IEEE Service Center, Piscataway, NJ, US, vol. 36, No. 1, Jan. 1, 2017 (Jan. 1, 2017), pp. 251-262.

Demene, et al., Spatiotemporal Clutter Filtering of Ultrafast Ultrasound Data Highly Increases Doppler and fUltrasound Sensitivity, IEEE Transactions on Medical Imaging, IEEE Service Center, Piscataway, NJ, US, vol. 34, No. 11, Nov. 1, 2015 (Nov. 1, 2015), pp. 2271-2285.

Yoo, et al., Adaptive clutter filtering for ultrasound color flow imaging, Ultrasound in Medicine and Biol, New York, NY, US, vol. 29. No. 9, Sep. 1, 2003, pp. 1311-1320.

\* cited by examiner

METHODS FOR SUPER-RESOLUTION ULTRASOUND IMAGING OF MICROVESSELS

CROSS-REFERENCE TO RELATED APPLICATIONS

This application is a 371 U.S. National Phase application of PCT/US2018/035147, filed on May 30, 2018, which claims the benefit of U.S. Provisional Patent Application Ser. No. 62/512,847, filed on May 31, 2017, and entitled "METHODS FOR SUPER-RESOLUTION ULTRASOUND IMAGING OF MICROVESSELS," each of which is herein incorporated by reference in its entirety.

BACKGROUND

Ultrasound contrast microbubbles are routinely used in clinic for ultrasound imaging enhancement. The typical size of a microbubble ranges between 1-5 µm, which is much smaller than the wavelength of ultrasound, which is typically on the order of 100-800 µm. As a result, single microbubbles appear as blurred point sources with a similar size as the ultrasound wavelength. Also, microbubbles that are less than half an ultrasound wavelength apart cannot be resolved individually, a consequence that is referred to as the diffraction limit of ultrasound.

A common scheme to break the diffraction limit of an imaging system is to create isolated point sources that are at least half of an ultrasound wavelength apart from each other, and to use the center location of these blurred point sources (e.g., the location where the maximum intensity value of the blurred point source is) to form images. There is a significant challenge, however, in achieving this localization-based super-resolution imaging to obtain isolated point sources.

In ultrasound imaging, two methods have been recently proposed to address this challenge. The first method facilitates microbubble isolation by diluting the microbubble solutions. The second method uses high frame-rate ultrasound to monitor the "blinking" events of microbubbles, which can isolate individual microbubble signals from a crowd of microbubbles. To achieve super-resolution imaging and obtain hemodynamics measurements, both of these methods rely on robust microbubble tracking and accumulation techniques to form microvessel images. However, microbubble tracking and accumulation can be susceptible to noise and tissue motion.

Thus, there remains a need for super-resolution processing methods that can significantly improve microbubble tracking and accumulation.

SUMMARY OF THE DISCLOSURE

The present disclosure addresses the aforementioned drawbacks by providing a method for super-resolution imaging of microvessels using an ultrasound system. Ultrasound data that were acquired with an ultrasound system from a region-of-interest in a subject in which a microbubble contrast agent was present when the ultrasound data were acquired are provided to a computer system. Microbubble signal data are generated with the computer system by isolating microbubble signals in the ultrasound data from other signals in the ultrasound data. Microbubbles are localized in the microbubble signal data by processing the microbubble signal data with the computer system to determine spatial locations associated with microbubbles in the microbubble signal data. A super-resolution microvessel image is produced based at least in part on the localized microbubble signals.

It is another aspect of the present disclosure to provide a method for producing with an ultrasound system, an image indicating microbubbles that have been tracked through time. Ultrasound data are acquired from a region-of-interest in a subject in which a microbubble contrast agent was present when the ultrasound data were acquired. The ultrasound data have at least one spatial dimension and at least one temporal dimension comprising a plurality of time frames. Microbubble signal data are generated with a computer system by processing the ultrasound data to isolate microbubble signals from other signals in the ultrasound data. Microbubbles are localized in the microbubble signal data with the computer system by processing the microbubble signal data to determine spatial locations of microbubbles in each of the time frames. Tracked microbubble data are generated by globally tracking the spatial locations of the microbubbles along the temporal dimension by pairing spatial locations of microbubbles in different time frames. An image is produced based on the tracked microbubble data.

It is another aspect of the present disclosure to provide a method for producing an image depicting microbubbles with an ultrasound system. A spatially sparse image that depicts microbubbles in a region-of-interest in a subject is provided to a computer system. The spatially sparse image is inputted to a sparsity-promoting signal estimation cost function that includes at least one sparsity-promoting term and at least one data-fidelity term. An updated image is produced with the computer system by minimizing the sparsity-promoting signal estimation cost function in order to estimate signals associated with microbubbles not depicted in the spatially sparse image. The updated image is stored for later use.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for super-resolution ultrasound imaging of microvessels in a subject. Ultrasound data are acquired from a region-of-interest in a subject who has been administered a microbubble contrast agent. The ultrasound data are acquired while the microbubbles are moving through, or otherwise present in, the region-of-interest. The region-of-interest may include, for instance, microvessels or other microvasculature in the subject. By isolating, localizing, tracking, and accumulating the microbubbles in the ultrasound data, super-resolution images of the microvessels can be generated, as described in the present disclosure.

Figure 1:
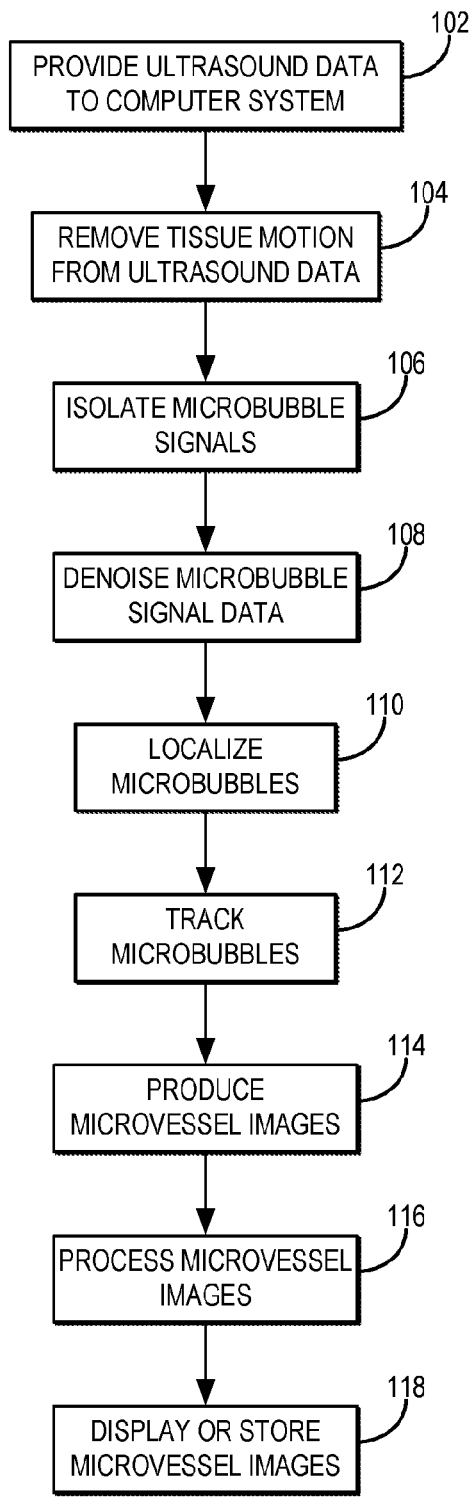
FIG. 1 is a flowchart setting forth the steps of an example method for producing super-resolution images of a microvessel with an ultrasound system.

Referring now to FIG. 1, a flowchart is illustrated as setting forth the steps of an example method for using an ultrasound system to produce super-resolution images of microvessels in a subject who has been administered a microbubble contrast agent. In general, super-resolution refers to a resolution that is enhanced relative to the resolution attainable with the imaging system. For instance, super-resolution ultrasound images can refer to images with resolution that is finer than the diffraction limit.

The method includes providing ultrasound data to a computer system, as indicated at step 102. In some embodiments, providing the ultrasound data to the computer system can include retrieving previously acquired ultrasound data from a memory or other data storage, which may be a part of or separate from the computer system. In some other embodiments, providing the ultrasound data can include acquiring such data with an ultrasound system and providing the acquired data to the computer system, which may be a part of or separate from the ultrasound system.

The ultrasound data can be ultrasound radiofrequency data, ultrasound in-phase quadrature ("IQ") data, or the like. In general, the ultrasound data contains one or more spatial dimensions, which may include a lateral dimension, an axial dimension, an elevational dimension, and combinations thereof. For instance, the ultrasound data can contain two spatial dimensions, such as the lateral and axial dimensions. The ultrasound data may also contain a temporal dimension, such as a dimension in slow time (i.e., the temporal direction along which multiple ultrasound signals are collected).

In some embodiments, the ultrasound data are acquired in a manner that promotes localization of microbubbles, such as by using a diluted microbubble solution, a high frame-rate monitoring of the "blinking" microbubble events, or other such methods that can produce isolated microbubble sources.

As stated above, the ultrasound data are acquired from a subject who has been administered a microbubble contrast agent. In some embodiments, different microbubbles (e.g., microbubbles with different sizes) with different resonant ultrasound frequencies can be used for imaging, so that by selecting a specific ultrasound frequency (e.g., either transmit or receive at a specific frequency), only a subgroup of selected microbubbles will be imaged, thereby forming ultrasound data containing isolated microbubble sources. As another example, an ultrasound pulse that has sufficient energy to rupture a certain number of microbubbles can be used, wherein the ruptured microbubbles then release the free gas bubbles from the microcapsule and generate ultrasound signals that have different amplitude than the intact microbubbles. This effectively creates isolated microbubble sources that can be used for super-resolution imaging.

The microbubble signal can be obtained from both the linear and nonlinear components of the ultrasound wave. The linear component is typically at the fundamental frequency of the applied ultrasound wave, while the nonlinear component can be at both the harmonic frequencies of the applied ultrasound wave, at the fundamental frequency of the applied ultrasound wave, or both. For instance, the nonlinearity introduced by amplitude-modulation-base imaging methods can be at the fundamental frequency.

The ultrasound data are processed to remove tissue motions, as indicated at step 104. For in vivo imaging, transducer movement and tissue motion induced by the cardiovascular (e.g., heart beat and pulsatile motion from arteries) and respiratory systems can be present. The amplitude of these motions can be significantly larger than the size of the microvessel to be resolved, thereby introducing significant blurring of the microvessel images and causing inaccurate blood flow speed measurements. Therefore, the ultrasonically detected microbubble signal can be processed to remove these tissue motions.

Figure 2:
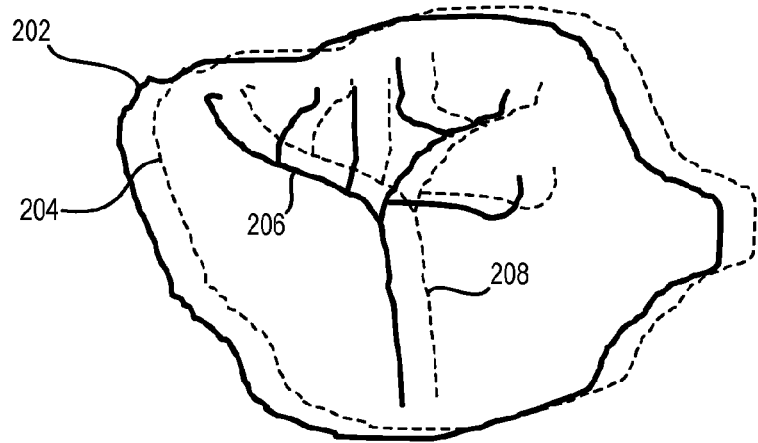
FIG. 2 depicts an example of microvessels that move between consecutive time frames as a result of tissue motion.

As one example, the ultrasound data can be processed to realign spatially misregistered microbubble signals that are from the same microvessel location. For example, as shown in FIG. 2, due to physiological motion such as breathing, the tissue 202 is moved to a different tissue location 204 and the targeted microvessel 206 is moved to a different microvessel location 208. If unaccounted for, this misregistration (i.e., the movement) will cause errors in the accumulation and tracking of microbubbles.

To correct for the misregistration caused by tissue motion, image registration and tissue motion compensation methods can be used. For example, an image intensity-based image registration method, such as an affine transformation, can be used to translate, rotate, scale, and shear a misregistered image back to the original location. Other image registration methods that can be used include an image-feature based image registration, a spectral-phase based image registration method, a transform model based image registration, and so on. As another example, an ultrasound speckle tracking-based method, such as two-dimensional normalized cross-correlation, can be used to estimate the movement vector between the reference signals and the moved tissue and microvessel signals. The signals can then be realigned by reversing the movement based on the estimated movement vector. As yet another example, a two-dimensional phase-shift map can be estimated between the reference image and the moved image, which can then be applied to the Fourier domain to the moved image followed by an inverse Fourier transform to correct for the movement. As one non-limiting example, the microbubble signal registration process is performed between each frame of ultrasound microbubble signal and a reference frame of microbubble signal (e.g., the first frame of the imaging sequence). Due to the high frame rate acquisition of ultrasound data, the estimate tissue motion can be generally assumed to be smooth along the temporal direction without sharp peaks that would otherwise indicate fast tissue movement that are physiologically realistic. This characteristic of the tissue motion can be used to suppress false peaks of the tissue motion estimation and, thus, minimize misregistrations.

Referring again to FIG. 1, after tissue motions are removed from the ultrasound data, microbubble signals are isolated in the ultrasound data, as indicated at step 106. In general, isolating the microbubbles signals includes isolating microbubble signals from the background signals, such as tissue signal and signals from non-changing microbubbles that do not change between acquisition frames (e.g., when a microbubble that does not move between frames). In some embodiments, the microbubble signals can be isolated using a frame-to-frame signal subtraction, a high-pass filtering along the temporal direction of the signal, a singular value decomposition ("SVD")-based filtering, and so on.

As one example, temporal high-pass filtering can be used to isolate microbubble signals. In these implementations, a cutoff frequency that is lower than the temporal frequency of the isolated microbubble signal, but higher than that of background signal can be used to filter the ultrasound data to isolate microbubble signals.

As another example, an SVD-based filtering can be used, in which a singular value cutoff can be used to separate the background signal (e.g., the tissue signal and non-moving microbubble signal, which are typically projected to low-order singular values) from the isolated moving microbubble signals (which are typically projected to intermediate-to-high-order singular values). As one example, the block-wise adaptive SVD filter described in co-pending PCT Application No. PCT/US2017/016190, which is herein incorporated by reference in its entirety, can be used to implement an SVD-based filtering to extract the microbubble signals. As another example, the accelerated SVD filter described in co-pending U.S. Provisional Patent Application No. 62/454,213, which is herein incorporated by reference in its entirety, can be used to implement an SVD-based filtering to extract the microbubble signals.

Optionally, the isolated microbubble signals can then be denoised, as indicated at step 108. The microbubble super-resolution imaging techniques described in the present disclosure are based, at least in part, on locating the center position of the microbubble. As such, removing the noise in each frame of the microbubble signal can help to more accurately localize and track the microbubbles.

In general, noise has similar features to microbubble signals, and it can be challenging to differentiate the two when the noise becomes stronger and the microbubble signal gets weaker in deeper regions of the tissue. As a result, noise signals can be falsely marked as microbubble signals, which results in inaccurate microbubble tracking and accumulation.

As one example, denoising can be implemented using an intensity-based thresholding method. Such methods are more accurate when it can be assumed that the microbubble signals are stronger than the background noise signals. For example, by suppressing pixels with intensity values less than a selected value (e.g., −30 dB to the maximum intensity value in the current field-of-view), a significant amount of background noise can be suppressed. However, these methods may not be as accurate in regions where microbubble signals are similar to noise (e.g., deep regions of the tissue). Also, the threshold value has to be carefully chosen to avoid falsely rejecting the microbubble signal or preserving too much noise.

As another example, the microbubble signals can be denoised based at least in part on the spatiotemporal information contained in the microbubble signals. Because microbubbles move with blood flow, the microbubble movements are deterministic events that can be continuously tracked in multiple acquisition frames, while noise events are random and will not show any track-like features across multiple acquisition frames. These differences between microbubbles and noise can be exploited in the spatiotemporal domain for robust noise suppression. As an example, a non-local means ("NLM") denoising filter can be applied to the original, noisy microbubble data.

Another advantage of the spatiotemporal denoising filter described above is that because the denoising is performed in the spatiotemporal domain, there is little to no spatial blurring of the underlying microbubble signal. Other denoising methods (e.g., convolutional Gaussian smoothing, Gaussian spectral apodization, wavelet thresholding, or iterative total variation ("TV") minimization) can also be used in the spatiotemporal domain to achieve similar denoising effect. In some implementations, the axial-temporal microbubble signal data can be used for denoising, while in other implementations lateral-temporal data or full axial-lateral-temporal 3D data can also be used for denoising.

After the microbubble signal data are denoised, microbubbles are localized in the denoised microbubble signal data, as indicated at step 110. In general, this process includes identifying locations in each time frame of the microbubble signal data at which microbubbles are located. For instance, the center location of each isolated microbubble signal is located, such that the movement of the microbubble can be tracked through time. The center location of the localized microbubbles can also be used to construct super-resolution microvessel images and to track the movement of the microbubbles to calculate hemodynamics measurements, such as blood flow speed.

In some implementations, the microbubbles can be localized in the denoised microbubble signal data using deblurring and deconvolution methods, such as the CLEAN algorithm, sparsity or entropy-based iterative regression methods, a blind deconvolution method, and so forth.

Figure 3:
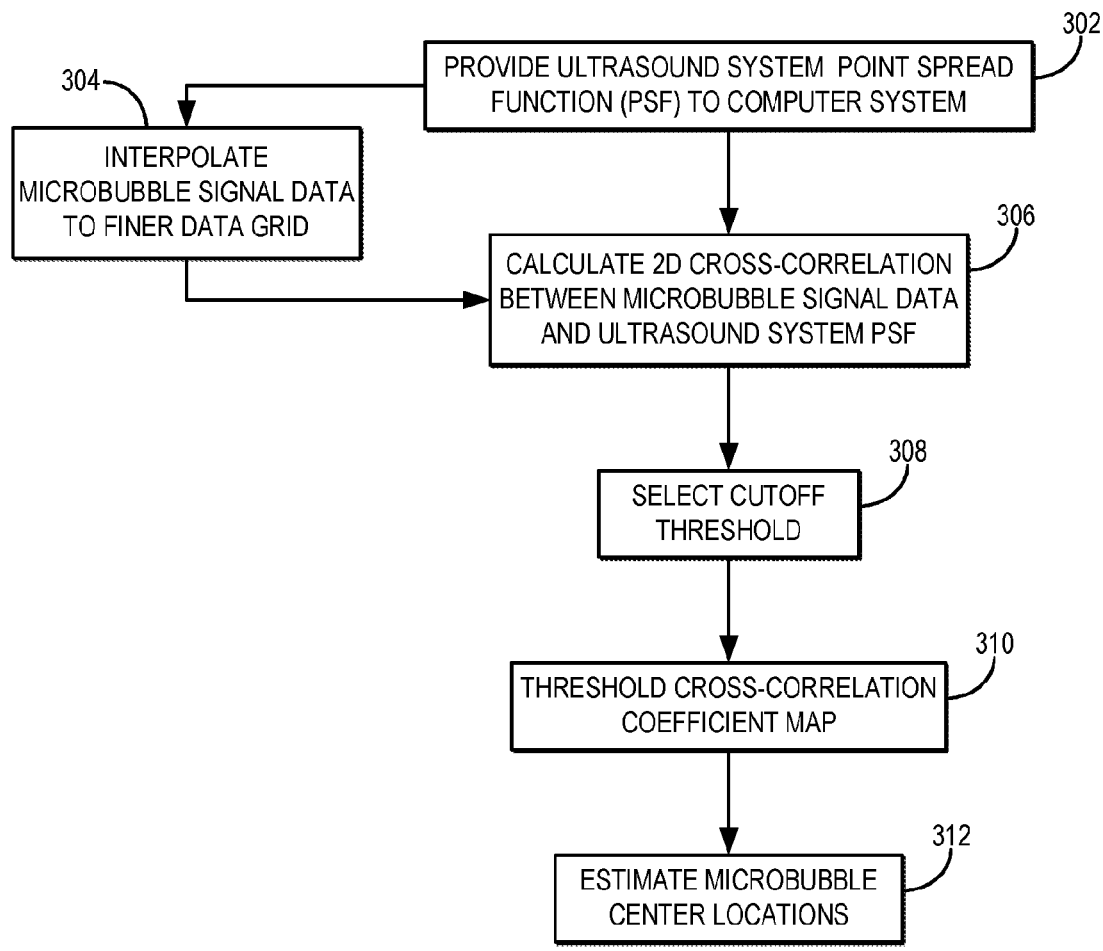
FIG. 3 is a flowchart setting forth the steps of an example method for isolating microbubble signals based on a cross-correlation with a point spread function of an ultrasound system.

In some other implementations, the microbubbles can be localized based on a two-dimensional normalized cross-correlation-based method that focuses on detecting structures with good correlation to the point-spread-function ("PSF") of the ultrasound system used to acquire the microbubble signal data. Referring now to FIG. 3, a flowchart setting forth the steps of one non-limiting example of such a method is now illustrated. This method includes providing a PSF associated with the ultrasound system to a computer system, such as the computer system being used to localize the microbubbles in the microbubble signal data, as indicated at step 302. Providing the PSF can include retrieving a previously computed or estimated PSF from a memory or other data storage, or can include computing or estimating the PSF as needed.

In one example, the PSF can be obtained from a simulation. For instance, the PSF can be simulated based on a multivariate Gaussian distribution. Such a distribution is useful because it can account for ultrasound lateral resolution that is typically coarser than the axial resolution; however, other distributions can also be used to simulate the PSF.

As another example, the PSF can be obtained from experimental measurements of a very small point object, such as an object that is much smaller than the ultrasound wavelength. For instance, the measured signal from a microbubble can be used as an approximation of the PSF of the ultrasound system.

To improve the accuracy of microbubble localization, the original microbubble signal data can be optionally interpolated to a finer data grid, as indicated at step 304. As an example, the microbubble signal data can be spatially interpolated by a selected amount, such as to ten times the original spatial resolution.

Figure 4:
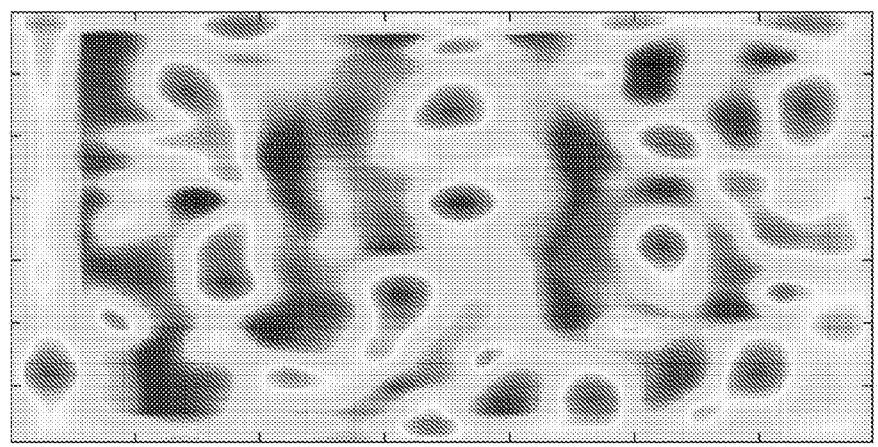
FIG. 4 is an example of a two-dimensional cross-correlation map computed between microbubble signal data and a point spread function of the ultrasound system used to obtain the microbubble signal data.

A two-dimensional normalized cross-correlation is calculated between the microbubble signal data, whether interpolated to a finer grid or not, and the provided ultrasound system PSF, as indicated at step 306. The result of this step is a 2D normalized cross-correlation coefficient map, an example of which is shown in FIG. 4. In the regions where there is better correlation between the detected microbubble signal and the ultrasound system PSF, the normalized cross-correlation coefficient will be higher.

Figure 5:
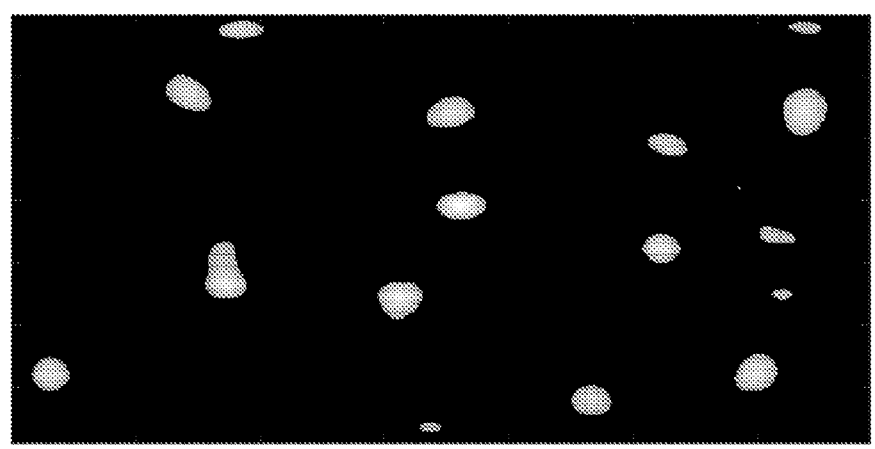
FIG. 5 is an example of microbubble signal data in which signals not associated with microbubbles has been rejected based on the two-dimensional cross-correlation map of FIG. 4.

By selecting a cross-correlation cutoff threshold, as indicated at step 308, the features that are not associated with microbubbles can be rejected to preserve the signals associated with the microbubbles, as indicated at step 310. An example of microbubble signal data in which the signals not associated with microbubbles have been rejected using this method is illustrated in FIG. 5.

Figure 6:
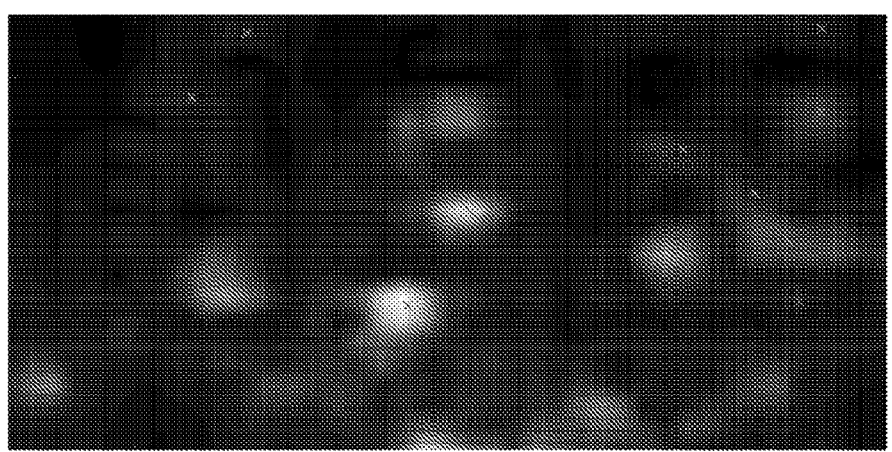
FIG. 6 is an example of center locations of microbubbles identified on the microbubble signal data of FIG. 5, where the center locations were determined by identifying local regional maxima in the two-dimensional cross-correlation map of FIG. 4.

The center location of each microbubble can then be estimated, as indicated at step 312. In some implementations, the center location can be estimated by identifying the local regional maximum of the thresholded cross-correlation coefficient map. In some other implementations, the center location can be estimated by performing a curve-fitting to the cross-correlation map to find the local maximum location. An example output of the localization is shown in FIG. 6, where the crosses indicate the estimated center locations of microbubbles. The localization process is conducted on each frame of the microbubble data until all microbubble events are identified and localized.

Referring again to FIG. 1, after the microbubbles are localized, their locations are accumulated and tracked, as indicated at step 112. In addition to being useful for producing super-resolved microvessel images and hemodynamics measurements, the microbubble tracking process can also provide a quality control step for the microbubble localization step. For instance, microbubble tracking can be used to reject false microbubble localizations from noise or unreliable microbubbles signals by removing localized microbubbles that cannot be tracked for a certain amount of time.

Figure 7:
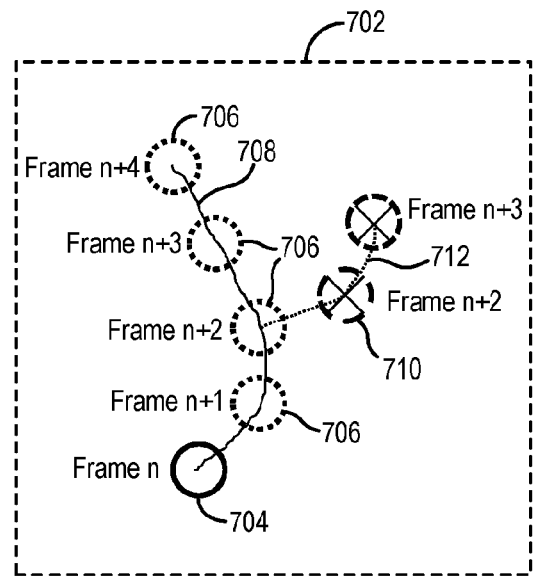
FIG. 7 depicts an example of tracking a microbubble location through a number of time frames using a local window in which errors can arise when other microbubbles are present in the same local window.

As one example, microbubble tracking can be implemented by locally tracking a single microbubble's movement. As shown in FIG. 7, this local tracking method typically uses a local window 702 to track a single microbubble's movement through time. As one example, two-dimensional cross-correlation can be used to track the microbubble's movement through time. The original microbubble signal in frame n 704 is tracked in frames n+1, n+2, n+3, and n+4, as indicated by dashed circles 706. The true microbubble movement trajectory is indicated by 708.

One drawback of this local window-based tracking method is that it is susceptible to other microbubble events that may occur in the same local tracking window 702. For example, another microbubble 710 may appear in the same local tracking window 702 in frames n+2 and n+3. It some instances, the microbubble tracking may be track this second microbubble 708, which may result in an incorrect microbubble movement trajectory indicated by 712. As a result, with local tacking methods complicated rules and models that can account for all possible situations (e.g., bubble birth, bubble death, new bubble appearance, bubble track merge, bubble track split) are generally established to robustly track microbubbles. The computational cost of these rules can, however, be prohibitive due to the large number of microbubbles that need to be individually tracked.

Figure 8:
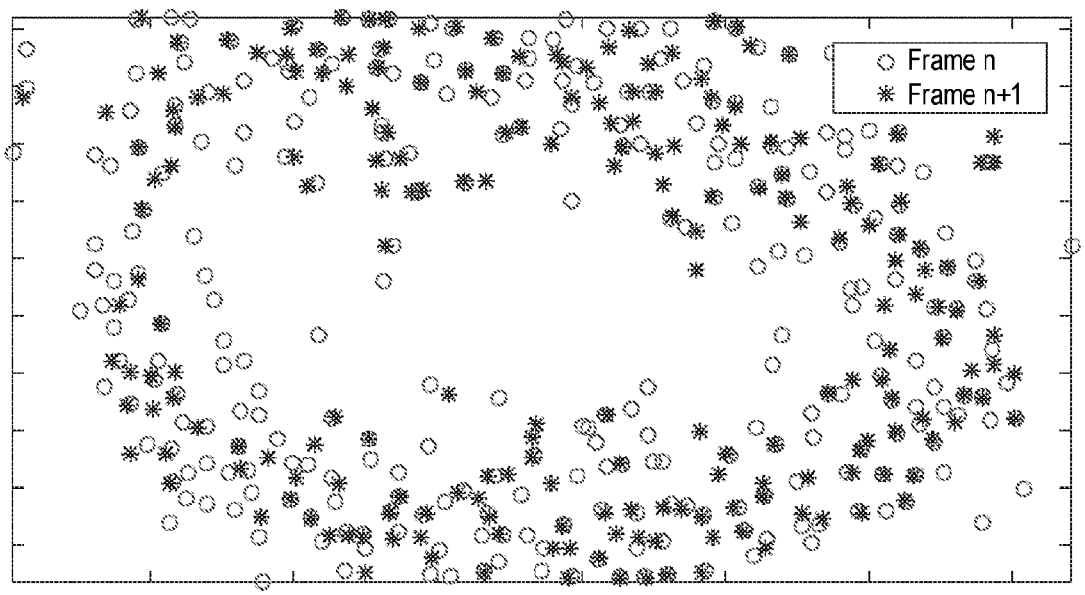
FIG. 8 is an example plot showing microbubble locations in a region-of-interest for two consecutive time frames.

Thus, in some embodiments of the methods described in the present disclosure, a global microbubble tracking method is implemented. As an example, the global tracking method can be based at least in part on a bipartite graph and minimal distance microbubble pairing. For illustrative purposes, an example of localized microbubble center locations for two consecutive frames (i.e., frame n and frame n+1) is shown in FIG. 8. The bipartite graph and minimal distance pairing described in the present disclosure is based on the principle that every true microbubble signal in frame n will have one and only one paired microbubble signal in frame n+1, and vice versa, and also that the total distance between all paired microbubbles should be minimum. This method is thus based on the assumption that the most probable location that the same microbubble in frame n will appear in frame n+1 is the location that is closest to where that microbubble was in frame n.

Figure 9:
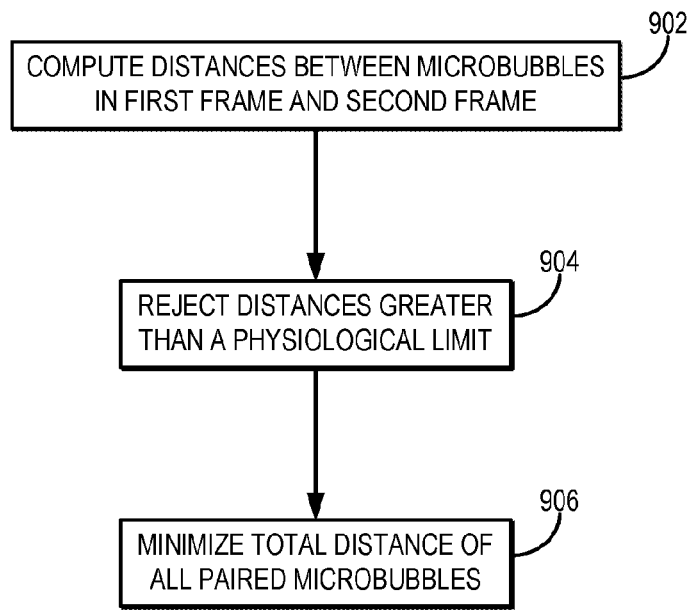
FIG. 9 is a flowchart setting forth the steps of an example method for pairing microbubble locations in consecutive time frames based on a bipartite graph and minimal distance pairing.
Figure 10:
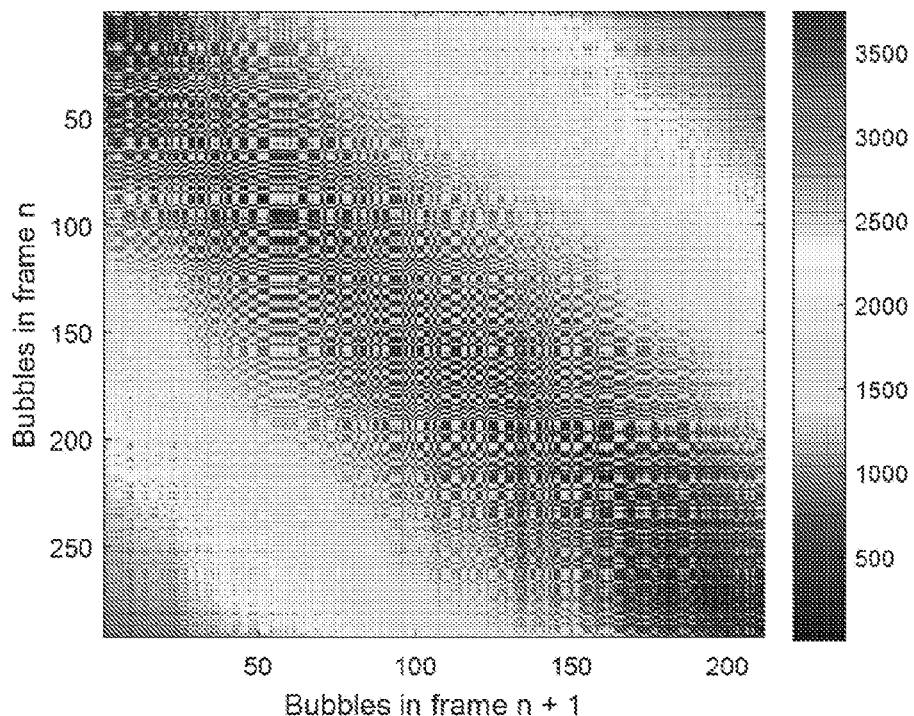
FIG. 10 is an example of a distance map depicting distances between pairs of microbubble locations in consecutive time frames of microbubble signal data.

Referring now to FIG. 9, a flowchart is illustrated as setting forth the steps of an example method for tracking microbubbles based on a bipartite graph and minimal distance pairing. The method includes calculating the distances between all microbubbles in a first frame and all microbubbles in a second frame, as indicated at step 902. As one example, the first and second frame can be temporally consecutive frames (e.g., frame n and frame n+1). In some other examples, the first and second frame do not need to be temporally consecutive, but can be different time frames. As a result, a distance map can be computed, such as the example distance map shown in FIG. 10. In this example distance map, the x-axis is the microbubble index number for all microbubbles in frame n+1, the y-axis is the microbubble index number for all microbubbles in frame n, and the value of each pixel in the distance map (indicated by the color scale bar) is distance in units of number of pixels.

Figure 11:
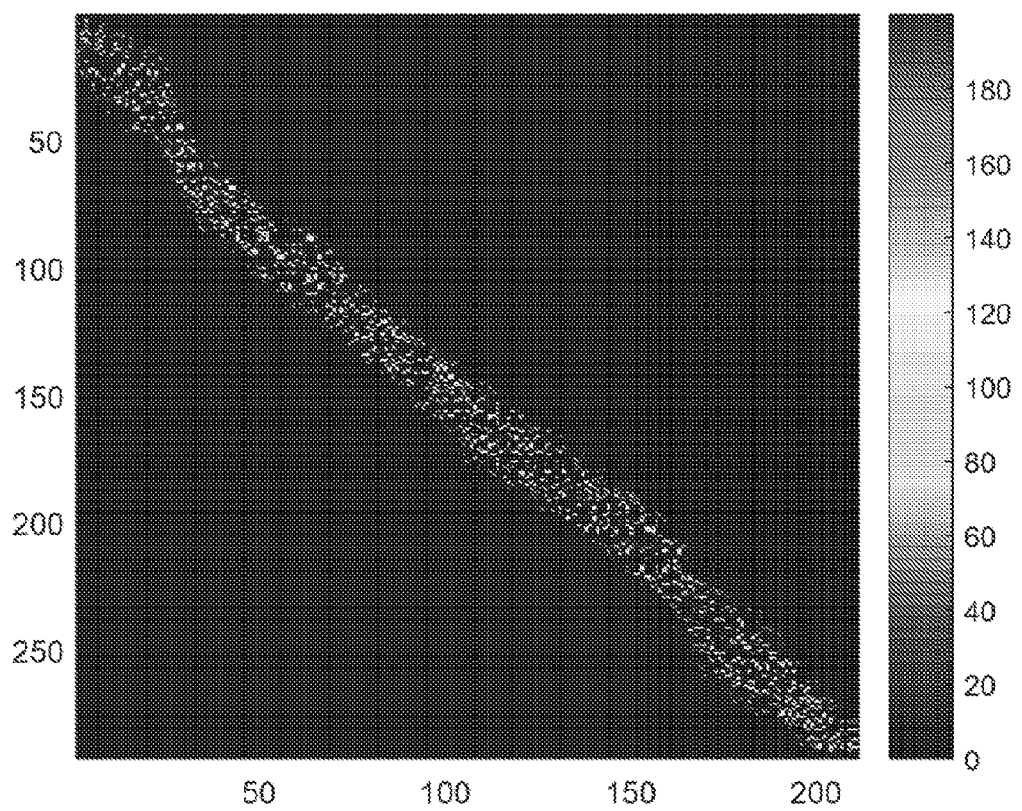
FIG. 11 is an example of the distance map of FIG. 10 after thresholding the distance map based on a physiological limit of blood flow.

Next, the distances between microbubbles that are beyond the physiologic limit of blood flow speed are rejected, as indicated at step 904. For instance, microbubbles cannot move over a certain distance within the time interval between two frames because the blood flow, which dictates the microbubble movement, cannot exceed a certain speed. As one example, a blood flow limit of 100 cm/s can be used. Applying this limit to the distance map in FIG. 10 results in the map shown in FIG. 11, where it can be seen that only a small portion of the original distance calculations is left, which is typically located around the distance matrix diagonal.

Figure 19:
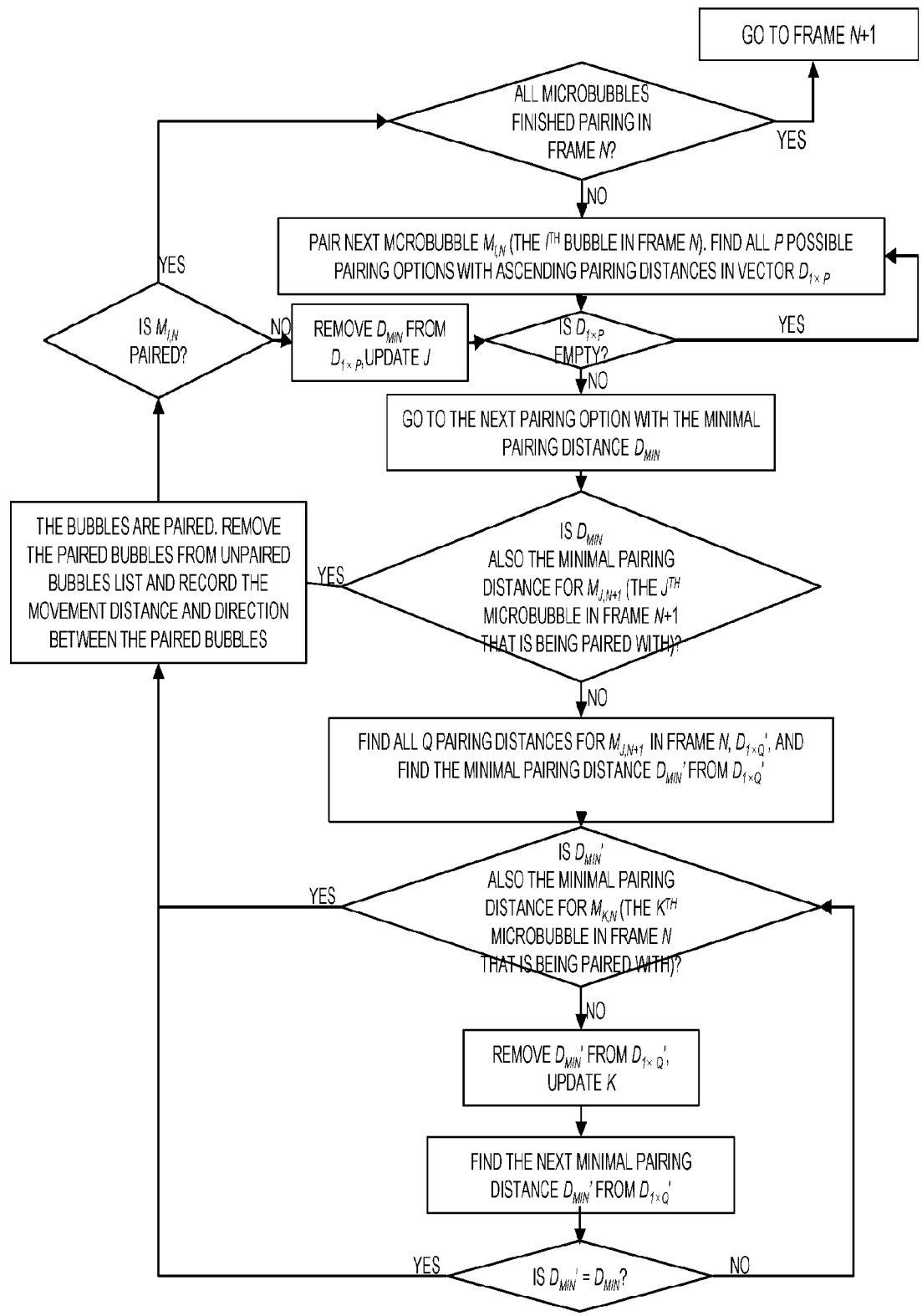
FIG. 19 is a flowchart setting forth the steps of an example partial assignment algorithm implementation of minimizing pairing distances between microbubbles.

The total distance of all paired microbubbles is then minimized, as indicated at step 906. For instance, the minimization problem can be based on the pairing distances in the thresholded distance map, such as the map shown in FIG. 11. As one non-limiting example, a partial assignment algorithm can be used to pair microbubbles based on minimal pairing distance. An example of a partial assignment algorithm implemented for this purpose is shown in FIG. 19. The basic principle behind the partial assignment algorithm implementation is that each microbubble will find a paired microbubble, the distance between which must be mutually minimal among all other pairing options of the two microbubbles. For instance, if microbubble A in frame n is being paired with a microbubble B in frame n+1, then the distance between A and B must be the smallest among all pairing distances for microbubble A with all microbubbles in frame n+1, and also the smallest among all pairing distances for microbubble B with all microbubbles in frame n. If a microbubble cannot be paired, then this microbubble signal is removed from future consideration (i.e., partial assignment). During the pairing process, the microbubble movement distance and direction can also be recorded for later hemodynamics measurements, such as blood flow speed. The bipartite graph and minimal distance pairing strategy is more accurate and computationally efficient than local tracking methods because the pairing process uses the information of all microbubbles in the field-of-view, and the pairing process can be operated on a simple two-dimensional matrix, such as the map shown in FIG. 11.

As another example, the pairing process can also be implemented as an assignment problem by assigning microbubbles in frame n to microbubbles in frame n+1, and vice versa. As one example of this type of implementation, a classic Hungarian algorithm (a.k.a. Kuhn-Munkres algorithm) can be used to arrive at an assignment solution.

Figure 12:
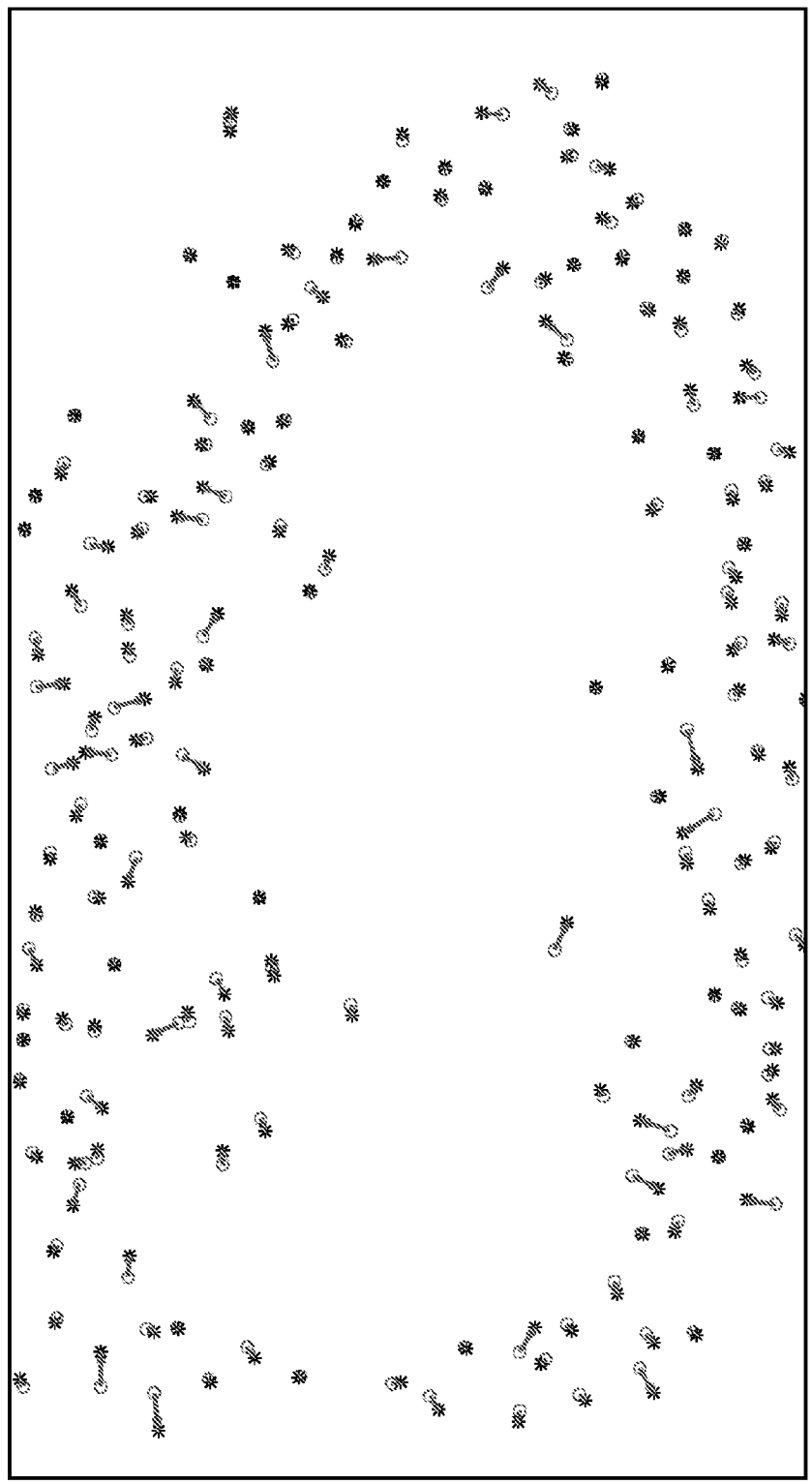
FIG. 12 an example plot showing paired microbubble locations in a region-of-interest for two consecutive time frames.

FIG. 12 shows one example of a bipartite graph global microbubble pairing result applied to the localized microbubble signals from FIG. 8. After pairing, many microbubble signals from FIG. 8 are rejected because they could not be paired. The microbubble movement distance and direction obtained during the pairing process are indicated by the length and the direction of the arrows, respectively.

After the bipartite graph minimal distance, or other, pairing process, a frame-to-frame pairing persistence control method can be used to further scrutinize the microbubble pairing and tracking results. For instance, it can be assumed that the same microbubble should be successfully paired in at least two or more consecutive frames to be counted as a reliable microbubble signal. Microbubble signals that cannot meet this persistence control criteria will be rejected.

Figure 13A:
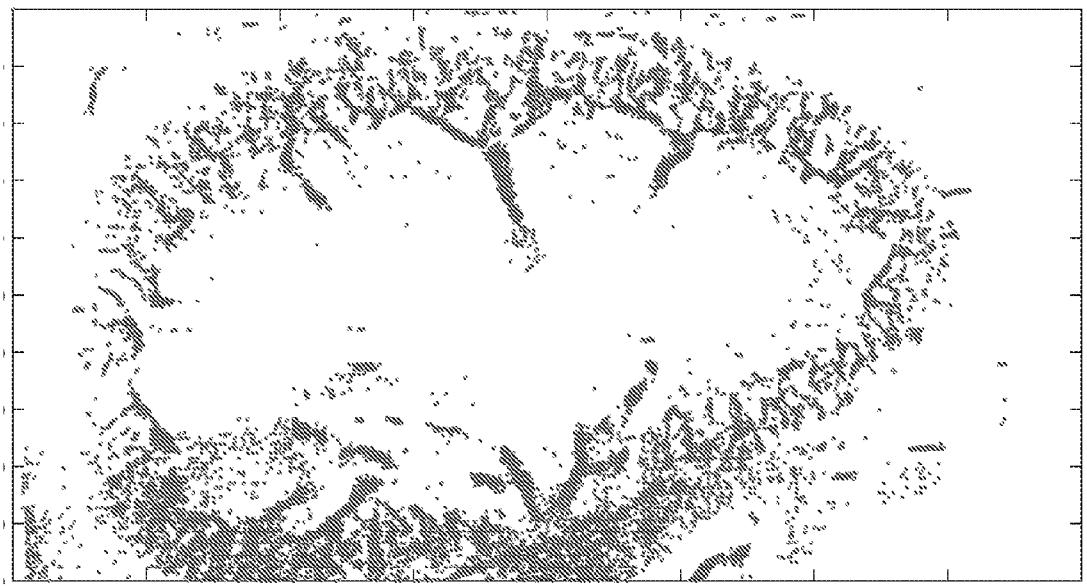
FIG. 13A is an example of an accumulated microbubble map before implementing a persistence control to remove spurious microbubble signals.
Figure 13B:
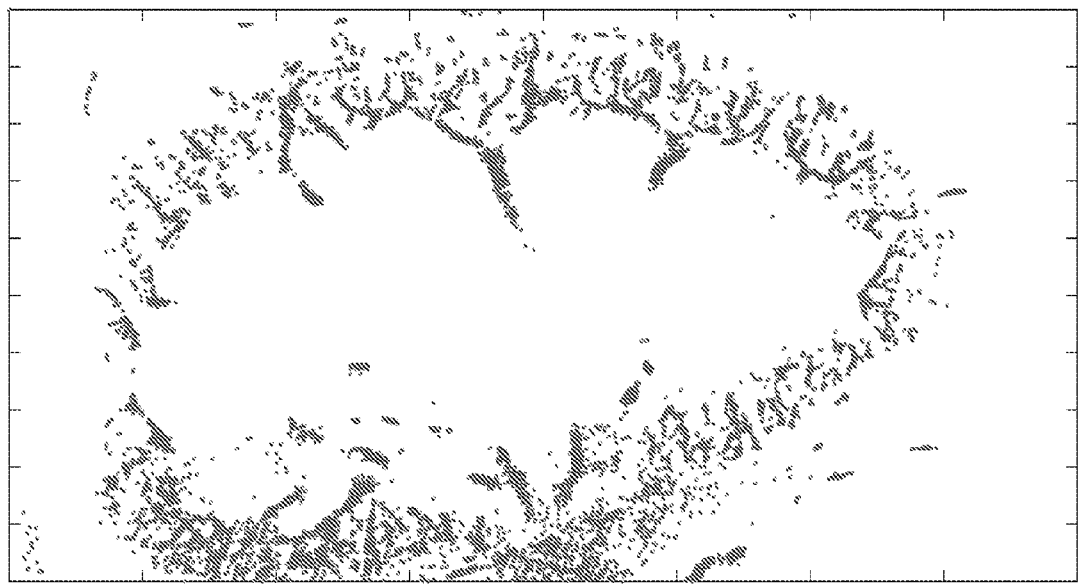
FIG. 13B is an example of the accumulated microbubble map of FIG. 13A after implementing a five frame-to-frame persistence control to remove spurious microbubble signals.

FIGS. 13A and 13B show an example result of a five frame-to-frame persistence control (i.e., the same microbubble has to be paired in at least five consecutive frames). FIG. 13A indicates an accumulated super-resolution microvessel image before persistence control, and FIG. 13B shows the result after persistence control. It can be seen in FIG. 13B that the persistence control method rejected many noise signals, especially in the deeper region of the tissue where noise is high.

The use of persistence control can also facilitate more robust blood flow speed estimates that are based on microbubble tracking. For example, after persistence control, any given microbubble can be successfully paired in n consecutive frames, where n>2 is the level of persistence control. Local blood flow speed and direction can be estimated by the movement distance and time interval between each pair of consecutive frames, resulting in blood flow speed measurements between each of the persistence controlled frames. These separate measurements can be combined to arrive at a more reliable estimate of the local blood flow speed. For example, the segment blood flow speed measurements can be averaged to obtain a mean blood flow speed for the microvessel, followed by assigning this blood flow speed value to all the pixels that the microbubble has travelled through. Alternatively, only the blood flow speed value can be assigned to the locations where the microbubble was actually located, which will result in a more sparse representation of the microvessel blood flow speed. As will be described below, this sparse blood flow speed map can then be processed to provide a more continuous microvessel image.

Referring again to FIG. 1, after the microbubbles have been localized and tracked in the microbubble signal data, one or more microvessel images are produced based on the localization and tracking results, as indicated at step 114. As one example, the microvessel image can include an accumulated microbubble location map throughout all of the acquisition frames. As another example, the microvessel image can include a blood flow speed map with blood speed values assigned to all the locations at which microbubbles were detected.

An accumulated microbubble location map depicts the number of times that a microbubble appeared at a certain location. Typically, larger vessels have more microbubbles flow through them during a given time interval, and thus will appear brighter than smaller vessels, which have fewer microbubbles flowing through them within the same time interval. In practice, when a more limited time interval is used for in vivo imaging because of physiological motion effects and microbubble dose limits, the resulting microbubble location map can be spatially sparse.

Figure 14:
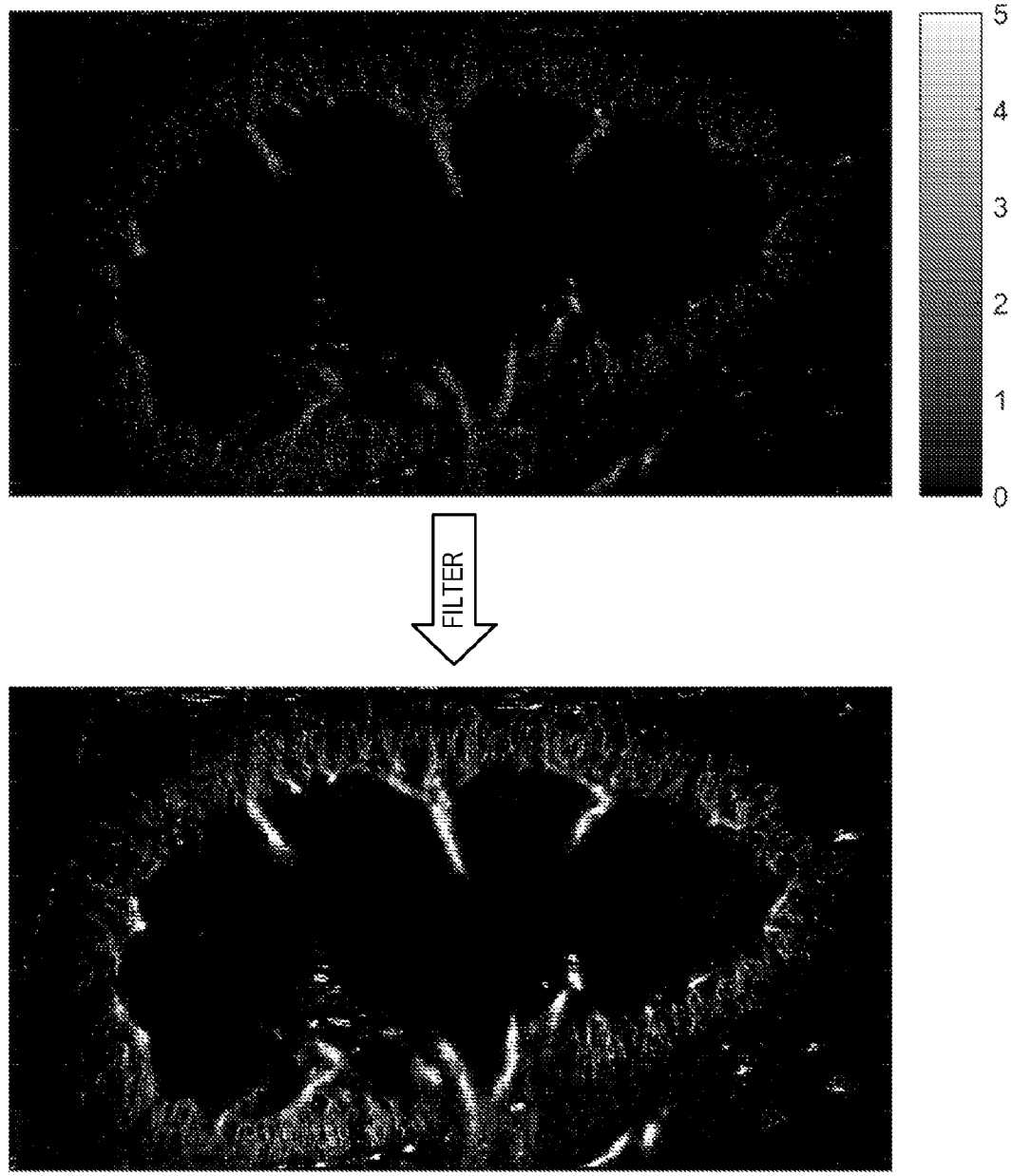
FIG. 14 depicts an example of filtering a microvessel in order to "inpaint" or "fill" blank regions among detected microbubble locations.

In such instances when the microvessel image (e.g., microbubble location map, blood flow map) is spatially sparse, the image can be processed to recover data, as indicated at step 116. As one example, a two-dimensional spatial low-pass filter (e.g., a 2D Gaussian smoothing filter) can be used to "fill" or "inpaint" the blank regions among detected microbubble locations. FIG. 14 shows an example of using a 2D Gaussian smoothing filter on a sparse microbubble location map. After filtering, the sparse microvessel pixels are better connected, which makes it easier to interpret the microvessel structure. Other spatial filters such as the median filter or a weighted averaging filter based on pixel intensity can also be used to obtain similar results.

One potential drawback of these local smoothing filter-based "filling" methods is that the final microvessel image can be blurred. These smoothing filters do not account for the morphological structure of the vessels or the underlying statistics of the microbubble data. It can therefore be difficult to recover the microvessel data without blurring the microvessel structure.

Thus, in some embodiments of the methods described in the present disclosure, a sparsity-promoting signal estimation method is used to process the microvessel location data. In this method, the microvessel data (i.e., the sparse microbubble location map) is treated as a corrupted version of the original data with missing data samples. A cost function minimization problem can be initialized, where the cost function includes a sparsity-promoting term and a data fidelity term. The underlying principle of this data recovery problem is that the ideal microvessel image will simultaneously exhibit sparsity (intrinsically, or in some transform domain) and, when passed through the forward system transform, should closely mirror the measured data set. Microvessel images can be sparsely represented using a variety of image processing transform methods, including wavelet transform, curvelet transform, Fourier transform, and singular value decomposition, and thus the sparsity-promoting term can include or otherwise be based on these operations. The sparsity-promoting term can also be learned using a machine learning algorithm, such as a K-SVD algorithm. The data fidelity term can be a simple difference measurement between the recovered data and the original data, or a statistically motivated term that aims to maximize the probability that the estimated signal gave rise to the observed data set (e.g., a likelihood function such as a Poisson distribution-based likelihood or a Gaussian distribution-based likelihood).

Figure 15:
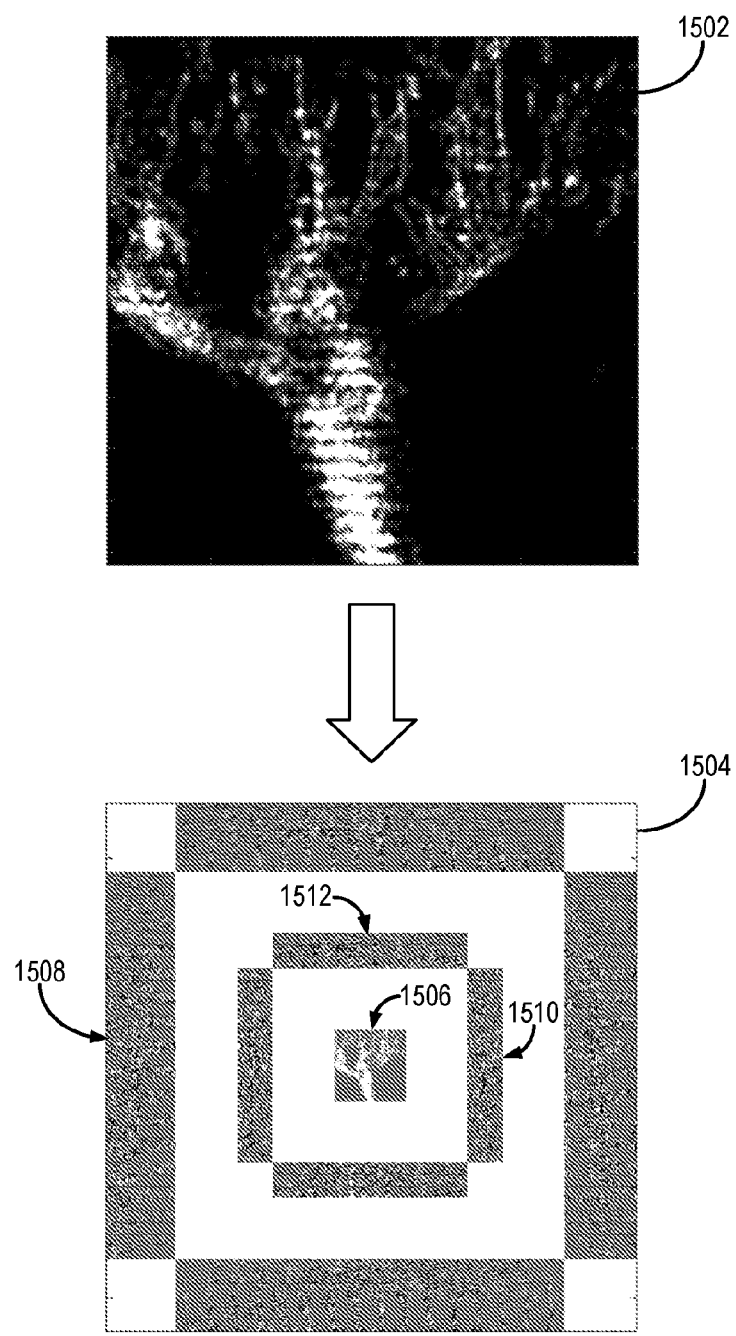
FIG. 15 depicts an example of a microvessel image and its corresponding 4-scale curvelet transform representation.

Thus, as one non-limiting example, a curvelet-based sparsity-promoting term and a Poisson distribution-based statistical data fidelity term can be used to achieve robust microvessel data recovery. In this example, for the data fidelity term, it is attempted to maximize the probability of observing the actual detected microvessel image provided the estimated microvessel image. For a Poisson probability distribution of the detected microvessel data samples, $y_i$, and the recovered microvessel data samples, $x_i$, then the probability of $P(x;y)$ (i.e., the probability of seeing exactly the detected y data samples when an average recovered data sample is x) is given by:

$$P(y;x) = \prod_i \frac{x_i^{y_i}}{y_i!} e^{-x_i}; \quad (1)$$

where i is the pixel index or a local block index of the microvessel data. Maximizing the probability term in Eqn. (1) can be viewed as minimizing the following, $$-\ln(P(x;y)) = -y^T \ln(x) + 1^T x + C \quad (2);$$

where C is a constant term that is generally irrelevant from an optimization perspective. The cost function, J(u), used for this microvessel data recovery problem can then be initialized as, for example, an analysis-type regularized regression:

$$\operatorname*{argmin}_u J(u) = \lambda \|\Phi u\|_1 + 1^T u - y^T \ln(u); \quad (3)$$

where $\Phi$ is the curvelet transform, and v are the curvelet coefficients. The curvelet transform decomposes the original microvessel data into different scales of curvelet coefficients that represent different directions and sizes of the microvessel structures. For example, as shown in FIG. 15, a scale-4 curvelet transform of a microvessel structure image 1502 gives the curvelet coefficients plot 1504. The inner portion 1506 of the curvelet coefficients plot 1504 represents larger microvessel structures with lower spatial frequencies, and the outer portion 1508 of the curvelet coefficients plot 1504 represents smaller microvessel structures with higher spatial frequencies. For example, from the direction of the central portion 1506 to the outer portion 1508, the curvelet coefficients represent smaller and smaller microvessel structures. The different quadrants of the curvelet coefficient plot 1504 represent microvessel structures growing in different directions. For example, region 1510 represents microvessel structures with lateral growing direction and region 1512 represents microvessel structures with axial growing direction.

Referring again to the minimization problem of Eqn. (3), the first term on the right hand side of the equation is the sparsity-promoting term, and the second and third terms are the data fidelity terms. The goal of minimizing the cost function is to achieve optimal data recovery. As one example, Eqn. (3) can be solved using an alternating direction method of multipliers ("ADMM") technique. With this approach, Eqn. (3) is first recast as a functionally equivalent constrained optimization problem, $$\operatorname*{argmin}_{u,v} J(u,v) = \lambda \|v\|_1 + 1^T u - y^T \ln(u), \text{ such that } v = \Phi u. \quad (4)$$

Subsequently the corresponding (e.g., scaled dual form) augmented Lagrangian functional of Eqn. (4) is constructed, which is given by:

$$L(u,v,\xi) = \lambda \|v\|_1 + 1^T u - y^T \ln(u) + \frac{\mu}{2} \|v - \Phi u - \xi\|_2^2. \quad (5)$$

To solve Eqn. (4), the saddle points of Eqn. (5) can be determined, which as one example can be efficiently achieved by performing the following Gauss-Seidel iteration until convergence:

$$u_{k+1} = \operatorname*{argmin}_u L(u, v_k, \xi_k) \quad (6)$$

$$v_{k+1} = \operatorname*{argmin}_v L(u_{k+1}, v, \xi_k)$$

$$\xi_{k+1} = \xi_k - (v_{k+1} - \Phi u_{k+1}).$$

For the first minimization term, the derivative of L (with respect to each pixel or a small local block with a collection of pixels) is taken respect to u and is forced to zero:

$$\left[\frac{\partial L}{\partial u}\right]_i = 1 - \frac{y_i}{u_i} + \mu \Phi^*(\Phi u_i - (v - \xi))_i = 0. \quad (7)$$

For a frequency wrapped curvelet transform, $\Phi^*\Phi = I$ (i.e., the adjoint and inverse curvelet operations are equivalent), Eqn. (7) can yield, $$\mu u_i^2 - (\mu \Phi^*(v - \xi)_i - 1) u_i - y_i = 0 \quad (8);$$

And therefore, $$u_{i,k+1} = \frac{\mu \Phi^*(v_k - \xi_k) - 1 + \sqrt{(\mu \Phi^*(v_k - \xi_k) - 1)^2 + 4\mu y}}{2\mu}. \tag{9}$$

For the second minimization, a soft-thresholding of the curvelet coefficient can be used, $$v_{k+1} = T_{\lambda/\mu}\{\Phi u_{k+1} + \xi_k\} \tag{10}.$$

Substituting Eqns. (9) and (10) into Eqn. (6) yields the following three iterative steps:

$$u_{k+1} = u_{i,k+1} = \frac{\mu \Phi^*(v_k - \xi_k) - 1 + \sqrt{(\mu \Phi^*(v_k - \xi_k) - 1)^2 + 4\mu y}}{2\mu} \tag{11}$$

$$v_{k+1} = T_{\lambda/\mu}\{\Phi u_{k+1} + \xi_k\}$$

$$\xi_{k+1} = \xi_k - (v_{k+1} - \Phi u_{k+1}).$$

Figure 16:
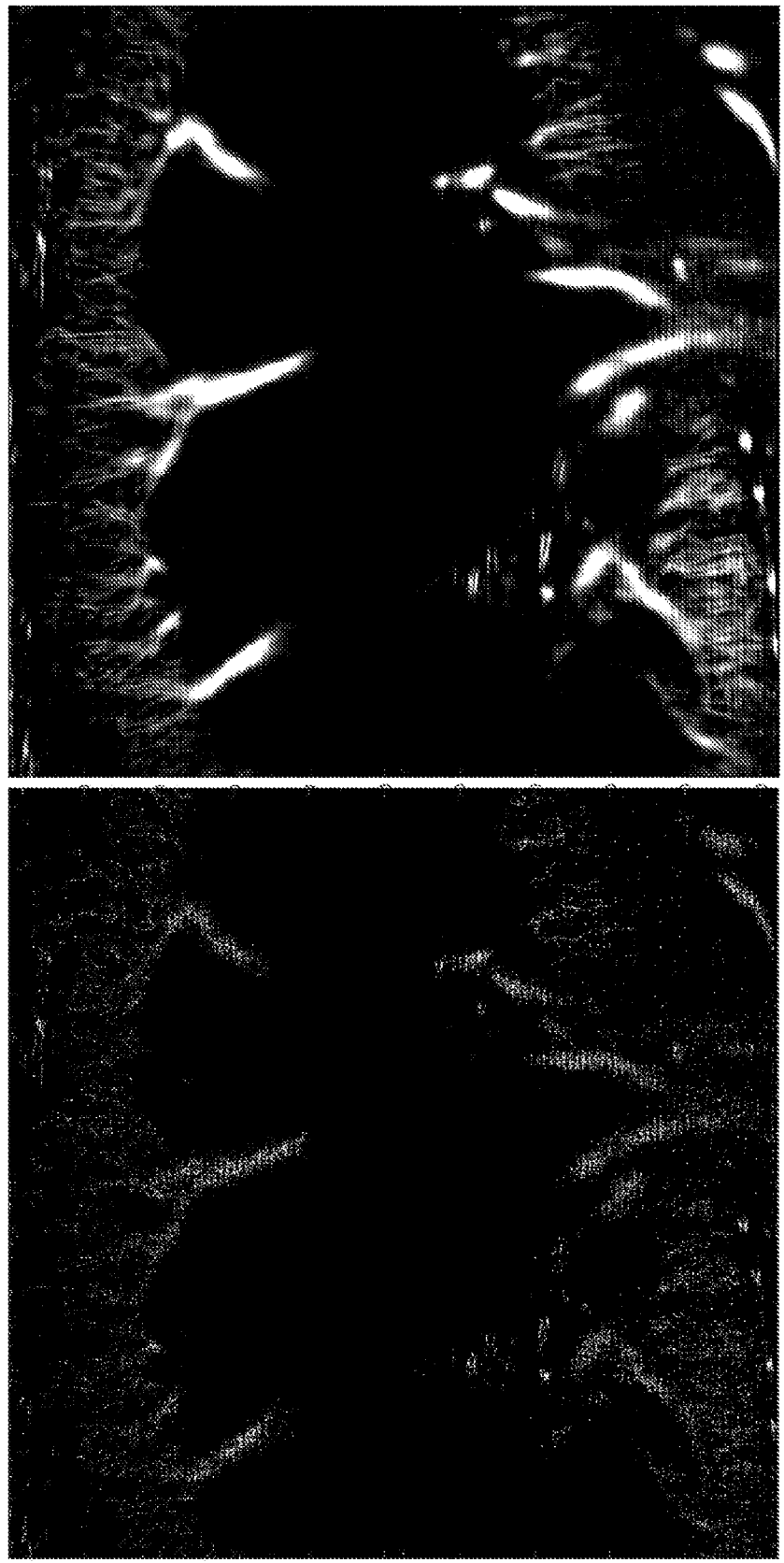
FIG. 16 depicts an example of a microvessel image before (left) and after (right) updating the microvessel image using a sparsity-promoting signal estimation.

FIG. 16 shows an example of an initial microvessel image 1602 and a microvessel image 1604 that has been processed with the data recovery technique described above. It can be seen that the data recovery method robustly recovers locations where the microvessel data are missing, without blurring the microvessel structures. In some implementations, the data recovery results can be further improved by applying constraints to the curvelet coefficient soft-thresholding step. For example, in the example shown in FIG. 16, most of the microvessel structure is growing along the top-to-bottom direction. Therefore, more curvelet coefficients that promote top-to-bottom microvessel structure direction (e.g., coefficients associated with region 1512, and the like, in FIG. 15) can be preserved and more curvelet coefficients corresponding to other microvessel structure directions can be rejected.

Referring again to FIG. 1, after processing, the microvessel images can be displayed to a user or stored for later use, such as for later analysis, as indicated at step 118. In some implementations, microvascular morphology measurements (e.g., vessel density and vessel tortuosity) can be estimated from the microvessel images. As another example, microvessel hemodynamics measurements (e.g., blood flow speed and blood flow volume) can be estimated from the microvessel images. For instance, the microvessel images can be superimposed, or presented side-by-side, with B-mode images of the targeted tissue. Alternatively, microvessel blood flow speed images with color-encoded flow direction can also be superimposed, or presented side-by-side, with B-mode images of the targeted tissue. In such implementations, a multi-flow-direction color hue can be used to indicate more than two directions of flow.

Vessel density can be calculated by selecting a region-of-interest on the microvessel image, from which the vessel density can be calculated by the total area (or total volume as in 3D imaging) of the vessel signal divided by the total area (or volume) of the region-of-interest. Vessel tortuosity can be measured by methods such as the distance metric, which provides a ratio of the actual path length of vessels normalized by linear distance between the vessel curve endpoints. The microvessel blood flow speed from the entire region-of-interest can be averaged to represent the perfusion index, or the blood flow speed can be integrated by the total cross-sectional area of the microvessel within the region-of-interest to derive a cross-sectional blood flow volume rate that can represent the perfusion index, or the blood flow speed from all microvessels can be used to generate a histogram (e.g., with x-axis representing blood flow speed and y-axis representing the total number of pixels with a certain blood flow speed in each x-axis bin) to represent the perfusion index.

The super-resolution microvessel image can also be displayed as dynamic video clips that show the dynamic microbubble movement to present the process of perfusion of a certain microvasculature. The movement of the microbubbles, which provides information of perfusion, can be monitored over time using such an approach. Another aspect of displaying a dynamic video dip is to use a different number of microbubble image frames to accumulate for different levels of microvessel details that can be dynamically displayed. For example, the more frames that are accumulated, the more microbubble movement tracks that can be visualized at a certain time instant. A high frame accumulation can be used to visualize slower flow vessels, and a low frame accumulation can be used to visualize faster flow vessels. Thus, by selectively choosing the number of frames to accumulate for a display, different blood flow speeds can be depicted and displayed to the user.

In addition to the methods described above for isolating microbubble signals, a microbubble control pulse can be implemented to modulate the microbubbles in a certain microvasculature so that isolated microbubble signals can be more readily obtained. As an example, the microbubble control pulse can implement higher transmit power ultrasound pulses (e.g., mechanical index>1.0) to disrupt microbubbles locally or globally to reduce the number of microbubbles, thereby increasing the chance of observing isolated microbubble signals.

The microbubble control pulse can include a series of focused ultrasound beams that are transmitted at localized or arbitrary locations within the field-of-view, which can be set by the user. As one example, a series of focused ultrasound beams targeted at a certain focal depth can be used. As another example, two series of focused ultrasound beams, which each series of focused ultrasound beams being targeted one of two different focal depths, can be used. The microbubble concentration control pulse can also include unfocused ultrasound beams, provided that the unfocused ultrasound beam has sufficient energy to modulate microbubbles.

Figure 17:
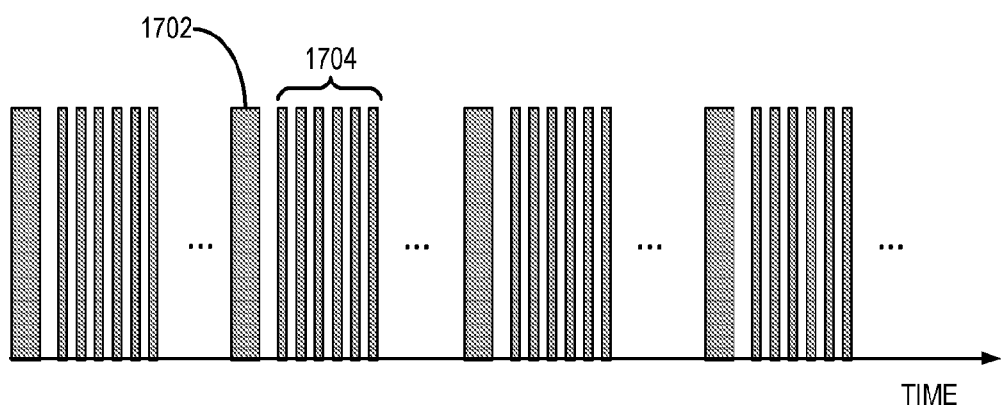
FIG. 17 is an example image sequence containing repeated applications of a microbubble control pulse followed by a series of detection pulses.

As shown in FIG. 17, the microbubble control pulse 1702 can be inserted into detection pulses 1704 to continuously modulate the microbubbles. A waiting time (e.g., several hundreds of microseconds) can be inserted right after the microbubble control pulse 1702 to attenuate ultrasound signals generated by the microbubble control pulse 1702. The power of the microbubble control pulse 1702 can be adjusted during the microbubble signal acquisition to maximize the amount of isolated microbubble signals. For example, for deeper microvessels or for obese patients, the power of the microbubble control pulse 1702 can be increased. The detected signals immediately before and after the microbubble control pulse 1702 can also be used to evaluate the efficacy of microbubble destruction or other modulation. For microvessels with depleted microbubble signals after the microbubble control pulse 1702, a timer can be set to record the time of arrival of the first microbubble signal at this microvessel, which can provide a perfusion speed estimate at a given microbubble concentration. The microbubble control pulse 1702 can also be useful in tissues such as liver where microbubble signals can be easily saturated by slow flow microvasculature.

Figure 18:
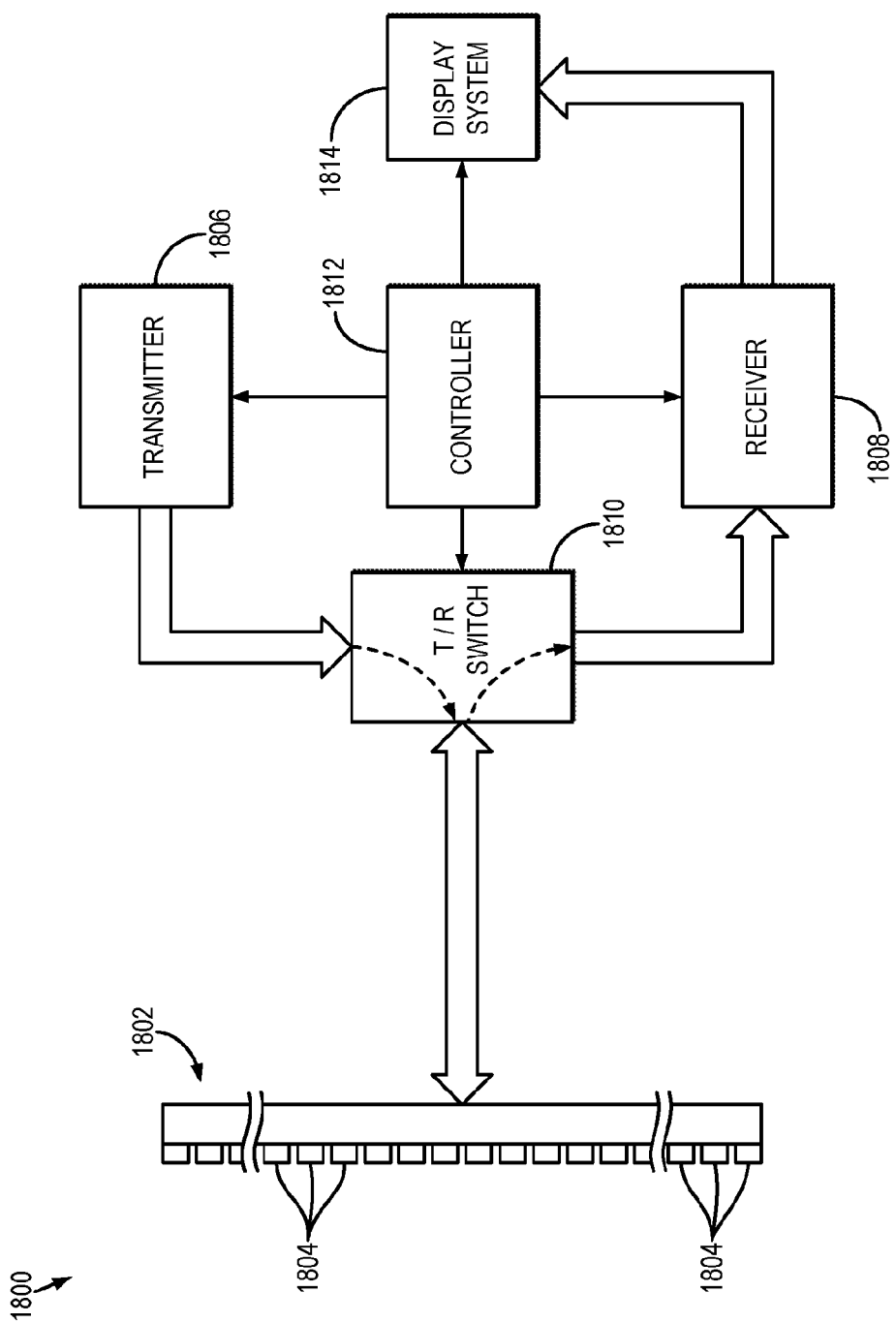
FIG. 18 is a block diagram of an example ultrasound system that can implement the methods described in the present disclosure.

FIG. 18 illustrates an example of an ultrasound system 1800 that can implement the methods described in the present disclosure. The ultrasound system 1800 includes a transducer array 1802 that includes a plurality of separately driven transducer elements 1804. The transducer array 1802 can include any suitable ultrasound transducer array, including linear arrays, curved arrays, phased arrays, and so on.

When energized by a transmitter 1806, each transducer element 1802 produces a burst of ultrasonic energy. The ultrasonic energy reflected back to the transducer array 1802 from the object or subject under study (e.g., an echo) is converted to an electrical signal (e.g., an echo signal) by each transducer element 1804 and can be applied separately to a receiver 1808 through a set of switches 1810. The transmitter 1806, receiver 1808, and switches 1810 are operated under the control of a controller 1812, which may include one or more processors. As one example, the controller 1812 can include a computer system.

The transmitter 1806 can transmit unfocused or focused ultrasound waves. In some configurations, the transmitter 1806 can also be programmed to transmit diverged waves, spherical waves, cylindrical waves, plane waves, or combinations thereof. Furthermore, the transmitter 1806 can be programmed to transmit spatially or temporally encoded pulses.

The receiver 1808 can be programmed to implement a suitable detection sequence for the imaging task at hand. In some embodiments, the detection sequence can include one or more of line-by-line scanning, compounding plane wave imaging, synthetic aperture imaging, and compounding diverging beam imaging.

Thus, in some configurations, the transmitter 1806 and the receiver 1808 can be programmed to implement a high frame rate. For instance, a frame rate associated with an acquisition pulse repetition frequency ("PRF") of at least 100 Hz can be implemented. In some configurations, the ultrasound system 1800 can sample and store at least one hundred ensembles of echo signals in the temporal direction.

The controller 1812 can be programmed to design an imaging sequence using the techniques described in the present disclosure, or as otherwise known in the art. In some embodiments, the controller 1812 receives user inputs defining various factors used in the design of the imaging sequence.

A scan can be performed by setting the switches 1810 to their transmit position, thereby directing the transmitter 1806 to be turned on momentarily to energize each transducer element 1804 during a single transmission event according to the designed imaging sequence. The switches 1810 can then be set to their receive position and the subsequent echo signals produced by each transducer element 1804 in response to one or more detected echoes are measured and applied to the receiver 1808. The separate echo signals from each transducer element 1804 can be combined in the receiver 1808 to produce a single echo signal. Images produced from the echo signals can be displayed on a display system 1814.

In some embodiments, the receiver 1808 may include a processing unit, which may be implemented by a hardware processor and memory, to process echo signals or images generated from echo signals. As an example, such a processing unit can isolate microbubble signals to produce microbubble signal data, localize microbubbles in microbubble signal data, track microbubble locations through time frames, accumulate microbubble locations, and produce microvessel images using the methods described in the present disclosure.

The present disclosure has described one or more preferred embodiments, and it should be appreciated that many equivalents, alternatives, variations, and modifications, aside from those expressly stated, are possible and within the scope of the invention.

The invention claimed is:

1. A method for super-resolution imaging of microvessels using an ultrasound system, the steps of the method comprising:
   (a) providing ultrasound data to a computer system, the ultrasound data having been acquired with an ultrasound system from a region-of-interest in a subject in which a microbubble contrast agent was present when the ultrasound data were acquired;
   (b) generating microbubble signal data with the computer system by processing the ultrasound data to isolate microbubble signals in the ultrasound data from other signals in the ultrasound data, the microbubble signal data comprising time frames of microbubble signal data;
   (c) localizing microbubbles in the microbubble signal data by processing the microbubble signal data with the computer system to determine spatial locations associated with microbubbles in the microbubble signal data in each time frame;
   (d) tracking the localized microbubbles in the microbubble signal data across time frames by minimizing a distance between microbubbles localized in consecutive time frames in order to track individual microbubbles; and
   (e) producing a super-resolution microvessel image based at least in part on the localized and tracked microbubble signals; and
   wherein producing the super-resolution microvessel image comprises:
     globally tracking the microbubbles as a function of time using a partial assignment in which localized microbubbles are paired one-to-one in consecutive time frames based on minimizing the distance between the microbubbles localized in consecutive time frames and unpaired microbubbles in each time frame are removed from consideration when producing the super-resolution microvessel image, and
     producing the super-resolution microvessel image based on the tracking of the microbubbles, wherein unpaired microbubbles in each time frame are not used when producing the super-resolution microvessel image.

2. The method as recited in claim 1, wherein isolating microbubble signals comprises removing background signals in the ultrasound data, wherein the background signals comprise signals associated with tissues and signals associated with stationary microbubbles.

3. The method as recited in claim 2, wherein removing the background signals comprises filtering the ultrasound data using a high-pass temporal filter in order to isolate microbubble signals in the ultrasound data.

4. The method as recited in claim 3, wherein the high-pass temporal filter comprises a cutoff frequency that is lower than a temporal frequency of the isolated microbubble signals and higher than a temporal frequency of the background signals.

5. The method as recited in claim 2, wherein removing the background signals comprises a frame-to-frame subtraction, in which temporally consecutive frames of the ultrasound data are subtracted to isolate microbubble signals while subtracting background signals.

6. The method as recited in claim 2, wherein removing the background signals comprises performing a singular value decomposition based filtering of the ultrasound data in order to in order to isolate microbubble signals in the ultrasound data.

7. The method as recited in claim 6, wherein a singular value cutoff value is selected to separate the background signals from the isolated microbubble signals, wherein the singular value cutoff value is greater than singular values associated with the background signals and lower than singular values associated with the isolated microbubble signals.

8. The method as recited in claim 1, wherein localizing microbubbles in the microbubble signal data comprises:
   providing to the computer system, a point spread function of the ultrasound system used to acquire the ultrasound data; and
   identifying the spatial locations of the microbubbles with the computer system based on a normalized cross-correlation between the microbubble signal data and the point spread function of the ultrasound system.

9. The method as recited in claim 8, wherein the point spread function is a simulated point spread function.

10. The method as recited in claim 9, wherein the simulated point spread function is simulated based at least in part on a multivariate Gaussian distribution.

11. The method as recited in claim 8, wherein the point spread function is estimated based on measurements obtained by imaging a small point object with the ultrasound system.

12. The method as recited in claim 11, wherein the small point object is smaller than an ultrasound wavelength used to image the small point object.

13. The method as recited in claim 12, wherein the small point object is a microbubble.

14. The method as recited in claim 8, wherein identifying the spatial locations of the microbubbles comprises:
   producing a cross-correlation map by computing the two-dimensional normalized cross correlation between microbubble signal data and the point spread function of the ultrasound system, the cross-correlation map depicting correlation coefficients between the microbubble signal data and the point spread function of the ultrasound system;
   removing entries in the cross-correlation map having correlation coefficients below a selected threshold value; and
   selecting the spatial locations of the microbubbles based on a local regional maximum of the correlation coefficients remaining in the cross-correlation map.

15. The method as recited in claim 1, wherein the spatial locations of the microbubbles are center locations of the microbubbles in each time frame of the ultrasound data.

16. The method as recited in claim 1, wherein isolating the microbubble signals comprises spatially interpolating the microbubble signal data to a finer spatial resolution before processing the microbubble signal data to isolate the microbubble signals.

17. The method as recited in claim 1, wherein globally tracking the microbubbles comprises performing a bipartite graph minimal distance pairing that pairs microbubbles between temporally consecutive image frames in the microbubble signal data.

18. The method as recited in claim 17, wherein performing the bipartite graph minimal distance pairing comprises:
   producing a distance map by calculating a distance between the spatial locations of each microbubble in a first image frame with the spatial locations of each microbubble in a second image frame;
   thresholding the distance map based on a physiological limit of blood flow speed; and
   minimizing a total distance of paired microbubbles.

19. The method as recited in claim 18, wherein the total distance of paired microbubbles is minimized based at least in part on a partial assignment algorithm that pairs microbubbles in the first image frame with microbubbles in the second image frame based on a minimal pairing distance.

20. The method as recited in claim 1, wherein globally tracking the microbubbles
   comprises pairing microbubbles in temporally consecutive image frames based on an optimized
   assignment solution that assigns microbubbles in a first image frame to microbubbles in a second image frame.

21. The method as recited in claim 20, wherein the optimized assignment solution is implemented as a Kuhn-Munkres algorithm.

22. The method as recited in claim 1, wherein globally tracking the microbubbles
   comprises pairing microbubbles in different image frames and performing a frame-to-frame persistence
   control on the paired microbubbles in order to scrutinize pairings of microbubbles.

23. The method as recited in claim 22, wherein the frame-to-frame persistence control rejects pairings of microbubbles that are not successfully paired in a selected number of temporally consecutive image frames.

24. The method as recited in claim 23, wherein the selected number of temporally consecutive image frames is at least two temporally consecutive image frames.

25. The method as recited in claim 23, wherein the selected number of temporally consecutive image frames is at least five temporally consecutive image frames.

26. The method as recited in claim 22, wherein the microvessel image depicts a measurement of local blood flow that is computed based on tracking microbubbles across the selected number of temporally consecutive image frames.

27. The method as recited in claim 1, further comprising processing the microvessel image to recover missing microvessel data.

28. The method as recited in claim 27, wherein recovering the missing microvessel data comprises applying a spatial low-pass filter to the microvessel image.

29. The method as recited in claim 27, wherein recovering the missing microvessel data comprises applying nonlinear averaging filters to the microvessel image.

30. The method as recited in claim 27, wherein recovering the missing microvessel data comprises inputting the microvessel image to a sparsity-promoting signal estimation.

31. The method as recited in claim 30, wherein the sparsity-promoting signal estimation comprises minimizing a cost function that includes a sparsity-promoting term and a data-fidelity term.

32. The method as recited in claim 31, wherein the sparsity-promoting term is based on at least one of a Fourier transform, a curvelet transform, a wavelet transform, or a singular value decomposition.

33. The method as recited in claim 31, wherein the sparsity-promoting term is empirically learned using a machine learning algorithm.

34. The method as recited in claim 33, wherein the machine learning algorithm comprises a K-SVD algorithm.

35. The method as recited in claim 31, wherein the data-fidelity term comprises measuring a difference between the inputted microvessel image and an updated microvessel image at each iteration of the sparsity-promoting signal estimation.

36. The method as recited in claim 31, wherein the data-fidelity term comprises maximizing a probability of observing the inputted microvessel image provided an estimated microbubble signal.

37. The method as recited in claim 36, wherein the estimated microbubble signal is based on a Poisson distribution likelihood functional.

38. The method as recited in claim 36, wherein the estimated microbubble signal is based on a Gaussian distribution likelihood functional.

39. The method as recited in claim 31, wherein the sparsity-promoting signal estimation is constrained with a constraint that promotes signal estimation along a specific spatial direction.

40. The method as recited in claim 1, wherein the microvessel image comprises an accumulated microbubble location map that depicts a number of times that a microbubble appeared at a given location in the region-of-interest.

41. The method as recited in claim 1, wherein the microvessel image depicts morphological measurements of a microvessel in the subject, wherein the morphological measurements comprise at least one of vessel density or vessel tortuosity.

42. The method as recited in claim 1, wherein the microvessel image depicts hemodynamics measurements of a microvessel in the subject, wherein the hemodynamics measurements comprise at least one of blood flow speed, perfusion indices derived from blood flow speed, or cross-sectional blood flow volume rate.

43. The method as recited in claim 1, further comprising denoising the isolated microbubble signal data before localizing the microbubbles.

44. The method as recited in claim 43, wherein denoising the microbubble signal data comprises denoising the microbubble signal data in a spatiotemporal domain.

45. The method as recited in claim 44, wherein denoising the microbubble signal data in the spatiotemporal domain comprises applying a non-local means filter to the microbubble signal data.

46. The method as recited in claim 44, wherein denoising the microbubble signal data in the spatiotemporal domain comprises applying a Gaussian smoothing filter to the microbubble signal data.

47. The method as recited in claim 44, wherein denoising the microbubble signal data in the spatiotemporal domain comprises applying a median filter to the microbubble signal data.

48. The method as recited in claim 1, further comprising processing the ultrasound data to remove tissue motion before isolating the microbubble signals, wherein the tissue motion is induced by at least one of transducer movement, the subject's cardiovascular system, or the subject's respiratory system.

49. The method as recited in claim 48, wherein processing the ultrasound data to remove tissue motion comprises computing a measurement of the tissue motion between one time frame of the ultrasound data and a reference frame of the ultrasound data, and realigning the two consecutive time frames of ultrasound data based on the measurement of the tissue motion.

50. The method as recited in claim 49, wherein measurement of the tissue motion is computed based on at least one of an image-intensity based image registration, an image-feature based image registration, a spectral-phase based image registration method, a transform model based image registration, or an ultrasound speckle tracking based method.

51. The method as recited in claim 49, wherein the reference frame of ultrasound data is a first frame of ultrasound data.

52. The method as recited in claim 1, wherein the provided ultrasound data comprises ultrasound data having at least two spatial dimensions and at least one temporal dimension.

53. The method as recited in claim 1, wherein the provided ultrasound data comprises ultrasound data acquired from both linear and nonlinear components of an ultrasound signal.

54. The method as recited in claim 1, wherein providing the ultrasound data comprises acquiring the ultrasound data from the subject using the ultrasound system.

55. The method as recited in claim 54, wherein acquiring the ultrasound data comprises applying a microbubble concentration control pulse that modulates a microbubble concentration in the region-of-interest in order to promote isolation of microbubble signals.

56. The method as recited in claim 55, wherein the ultrasound data are acquired using an imaging pulse sequence comprising the repeated application of:
 applying the microbubble concentration control pulse;
 waiting a waiting time during which no ultrasound pulses are applied;
 applying detection pulses after the waiting time to acquire the ultrasound data.

57. The method as recited in claim 56, wherein the waiting time is selected such that ultrasound signals generated by the microbubble concentration control pulse are sufficiently attenuated before the ultrasound data are acquired.

58. The method as recited in claim 56, wherein a power of the microbubble control pulse is adjusted during the imaging pulse sequence in order to maximize an amount of isolated microbubble signals in the acquired ultrasound data.

59. A method for super-resolution imaging of microvessels using an ultrasound system, the steps of the method comprising:
 (a) providing ultrasound data to a computer system, the ultrasound data having been acquired with an ultrasound system from a region-of-interest in a subject in which a microbubble contrast agent was present when the ultrasound data were acquired;
 (b) generating microbubble signal data with the computer system by processing the ultrasound data to isolate microbubble signals in the ultrasound data from other signals in the ultrasound data, the microbubble signal data comprising time frames of microbubble signal data;
 (c) localizing microbubbles in the microbubble signal data by processing the microbubble signal data with the computer system to determine spatial locations associated with microbubbles in the microbubble signal data in each time frame;
 (d) tracking the localized microbubbles in the microbubble signal data across time frames by minimizing a distance between microbubbles localized in consecutive time frames in order to track individual microbubbles; and
 (e) producing a super-resolution microvessel image based at least in part on the localized and tracked microbubble signals;

wherein producing the microvessel image comprises globally tracking the microbubbles as a function of time and producing the microvessel image based on that tracking of the microbubbles;

wherein globally tracking the microbubbles comprises performing a bipartite graph minimal distance pairing that pairs microbubbles between temporally consecutive image frames in the microbubble signal data; and wherein performing the bipartite graph minimal distance pairing comprises:
  producing a distance map by calculating a distance between the spatial locations of each microbubble in a first image frame with the spatial locations of each microbubble in a second image frame;
  thresholding the distance map based on a physiological limit of blood flow speed; and
  minimizing a total distance of paired microbubbles.

* * * * *

UNITED STATES PATENT AND TRADEMARK OFFICE
CERTIFICATE OF CORRECTION

PATENT NO. : 11,589,840 B2
APPLICATION NO. : 16/617628
DATED : February 28, 2023
INVENTOR(S) : Pengfei Song et al.

It is certified that error appears in the above-identified patent and that said Letters Patent is hereby corrected as shown below:

In the Specification

Column 14, Line 10, "video dip is" should be --video clip is--.

Signed and Sealed this
Eighteenth Day of April, 2023

Katherine Kelly Vidal
*Director of the United States Patent and Trademark Office*